(12) United States Patent
Byrd et al.

(10) Patent No.: US 9,029,376 B2
(45) Date of Patent: May 12, 2015

(54) SMALL MOLECULE INHIBITORS FOR THE TREATMENT OR PREVENTION OF DENGUE VIRUS INFECTION

(75) Inventors: Chelsea M. Byrd, Corvallis, OR (US);
Robert Jordan, Corvallis, OR (US);
Dongcheng Dai, Corvallis, OR (US);
Dennis E. Hruby, Albany, OR (US)

(73) Assignee: Siga Technologies, Inc., Corvallis, OR (US)

( * ) Notice: Subject to any disclaimer, the term of this patent is extended or adjusted under 35 U.S.C. 154(b) by 420 days.

(21) Appl. No.: 12/736,965

(22) PCT Filed: Jun. 2, 2009

(86) PCT No.: PCT/US2009/045921
§ 371 (c)(1),
(2), (4) Date: Mar. 18, 2011

(87) PCT Pub. No.: WO2009/149054
PCT Pub. Date: Dec. 10, 2009

(65) Prior Publication Data
US 2011/0158940 A1 Jun. 30, 2011

Related U.S. Application Data

(60) Provisional application No. 61/058,263, filed on Jun. 3, 2008.

(51) Int. Cl.
| A61K 31/4164 | (2006.01) |
| A61K 31/42 | (2006.01) |
| A61K 31/426 | (2006.01) |
| A61K 31/4184 | (2006.01) |

(52) U.S. Cl.
CPC ............. *A61K 31/42* (2013.01); *A61K 31/4164* (2013.01); *A61K 31/426* (2013.01); *A61K 31/4184* (2013.01)

(58) Field of Classification Search
CPC .. A61K 31/4164; A61K 31/42; A61K 31/426
USPC ....................................................... 514/235.5
See application file for complete search history.

(56) References Cited

U.S. PATENT DOCUMENTS

| 5,824,506 | A | * | 10/1998 | Chan et al. .................... 435/69.3 |
| 6,972,295 | B2 | * | 12/2005 | Hagmann et al. ............. 514/345 |
| 2004/0005304 | A1 | * | 1/2004 | Brudnak ...................... 424/93.45 |
| 2006/0194835 | A1 | | 8/2006 | DuGourd et al. |
| 2006/0246081 | A1 | | 11/2006 | Deem et al. |
| 2006/0270688 | A1 | | 11/2006 | Chong et al. |
| 2007/0265265 | A1 | | 11/2007 | Schmitz et al. |
| 2007/0281978 | A1 | | 12/2007 | Nakada et al. |
| 2008/0004277 | A1 | | 1/2008 | Chimmanamada et al. |

FOREIGN PATENT DOCUMENTS

| WO | WO2006093518 A2 | 9/2006 |
| WO | WO2007068380 A1 | 6/2007 |
| WO | WO2007103550 A2 | 9/2007 |
| WO | WO2007133108 A1 | 11/2007 |
| WO | WO 2007/139968 A2 | 12/2007 |

OTHER PUBLICATIONS

Supplementary European Search Report Application No. 09 75 9215.8, dated Feb. 8, 2012.
Barth, O. M. 1999. Ultrastructural aspects of the dengue virus (flavivirus) particle morphogenesis. J Submicrosc Cytol Pathol 31:407-12.
Benarroch, D., M. P. Egloff, L. Mulard, C. Guerreiro, J. L. Romette, and B. Canard. 2004. A structural basis for the inhibition of the NS5 dengue virus mRNA 2'-O-methyltransferase domain by ribavirin 5'-triphosphate. J Biol Chem 279:35638-43.
Brinton, M. A., and J. H. Dispoto. 1988. Sequence and secondary structure analysis of the 5'-terminal region of flavivirus genome RNA. Virology 162:290-9.
CDC. 2005. Dengue Fever, http://www2.ncid.cdc.gov/travel/yb/utils/ybGet.asp?section=dis&obj=dengue.htm.
Edelman, R., S. S. Wasserman, S. A. Bodison, R. J. Putnak, K. H. Eckels, D. Tang, N. Kanesa-Thasan, D. W. Vaughn, B. L. Innis, and W. Sun. 2003. Phase I trial of 16 formulations of a tetravalent live-attenuated dengue vaccine. Am J Trop Med Hyg 69:48-60.
Falgout, B., M. Pethel, Y. M. Zhang, and C. J. Lai. 1991. Both nonstructural proteins NS2B and NS3 are required for the proteolytic processing of dengue virus nonstructural proteins. J Virol 65:2467-75.
Fink, J., F. Gu, and S. G. Vasudevan. 2006. Role of T cells, cytokines and antibody in dengue fever and dengue haemorrhagic fever. Rev Med Virol 16:263-75.
Halstead, S. B. 1988. Pathogenesis of dengue: challenges to molecular biology. Science 239:476-81.
Hase, T., P. L. Summers, K. H. Eckels, and W. B. Baze. 1987. An electron and immunoelectron microscopic study of dengue-2 virus infection of cultured mosquito cells: maturation events. Arch Virol 92:273-91.
Hillen, W., G. Klock, I. Kaffenberger, L. V. Wray, and W. S. Reznikoff. 1982. Purification of the TET repressor and TET operator from the transposon Tn10 and characterization of their interaction. J Biol Chem 257:6605-13.

(Continued)

*Primary Examiner* — Yong Chong
(74) *Attorney, Agent, or Firm* — Ostrolenk Faber LLP

(57) ABSTRACT

Methods and pharmaceutical compositions for treating viral infections, by administering certain compounds in therapeutically effective amounts are disclosed. Methods of using the compounds and pharmaceutical compositions thereof are also disclosed. In particular, the treatment and prophylaxis of viral infections such as caused by flavivirus is disclosed, i.e., including but not limited to, Dengue virus, West Nile virus, yellow fever virus, Japanese encephalitis virus, and tick-borne encephalitis virus.

13 Claims, 1 Drawing Sheet

(56) References Cited

OTHER PUBLICATIONS

Kanesa-thasan, N., W. Sun, G. Kim-Ahn, S. Van Albert, J. R. Putnak, A. King, B. Raengsakulsrach, H. Christ-Schmidt, K. Gilson, J. M. Zahradnik, D. W. Vaughn, B. L. Innis, J. F. Saluzzo, and C. H. Hoke, Jr. 2001. Safety and immunogenicity of attenuated dengue virus vaccines (Aventis Pasteur) in human volunteers. Vaccine 19:3179-88.

Kitchener, S., M. Nissen, P. Nasveld, R. Forrat, S. Yoksan, J. Lang, and J. F. Saluzzo. 2006. Immunogenicity and safety of two live-attenuated tetravalent dengue vaccine formulations in healthy Australian adults. Vaccine 24:1238-41.

Koff, W. C., J. L. Elm, Jr., and S. B. Halstead. 1982. Antiviral effects if ribavirin and 6-mercapto-9-tetrahydro-2-furylpurine against dengue viruses in vitro. Antiviral Res 2:69-79.

Koff, W. C., R. D. Pratt, J. L. Elm, Jr., C. N. Venkateshan, and S. B. Halstead. 1983. Treatment of intracranial dengue virus infections in mice with a lipophilic derivative of ribavirin. Antimicrob Agents Chemother 24:134-6.

Leitmeyer, K. C., D. W. Vaughn, D. M. Watts, R. Salas, I. Villalobos, C. de, C. Ramos, and R. Rico-Hesse. 1999. Dengue virus structural differences that correlate with pathogenesis. J Virol 73:4738-47.

Malinoski, F. J., S. E. Hasty, M. A. Ussery, and J. M. Dalrymple. 1990. Prophylactic ribavirin treatment of dengue type 1 infection in rhesus monkeys. Antiviral Res 13:139-49.

Markoff, L., A. Chang, and B. Falgout. 1994. Processing of flavivirus structural glycoproteins: stable membrane insertion of premembrane requires the envelope signal peptide. Virology 204:526-40.

Medin, C. L., K. A. Fitzgerald, and A. L. Rothman. 2005. Dengue virus nonstructural protein NS5 induces interleukin-8 transcription and secretion. J Virol 79:11053-61.

Modis, Y., S. Ogata, D. Clements, and S. C. Harrison. 2003. A ligand-binding pocket in the dengue virus envelope glycoprotein. Proc Natl Acad Sci U S A 100:6986-91.

Monath, T. P. 1994. Dengue: the risk to developed and developing countries. Proc Natl Acad Sci U S A 91:2395-400.

Mukhopadhyay, S., R. J. Kuhn, and M. G. Rossmann. 2005. A structural perspective of the flavivirus life cycle. Nat Rev Microbiol 3:13-22.

Paho. 2006. Dengue and dengue hemorrhagic fever http://www.paho.org/english/ad/dpc/cd/dengue.htm.

Raviprakash, K., M. Sinha, C. G. Hayes, and K. R. Porter. 1998. Conversion of dengue virus replicative form RNA (RF) to replicative intermediate (RI) by nonstructural proteins NS-5 and NS-3. Am J Trop Med Hyg 58:90-5.

Rothman, A. L., and F. A. Ennis. 1999. Immunopathogenesis of Dengue hemorrhagic fever. Virology 257:1-6.

Sabcharoen, A., J. Lang, P. Chanthavanich, S. Yoksan, R. Forrat, P. Attanath, C. Sirivichayakul, K. Pengsaa, C. Pojjaroen-Anant, W. Chokejindachai, A. Jagsudee, J. F. Saluzzo, and N. Bhamarapravati. 2002. Safety and immunogenicity of tetravalent live-attenuated dengue vaccines in Thai adult volunteers: role of serotype concentration, ratio, and multiple doses. Am J Trop Med Hyg 66:264-72.

Schlesinger, S., and M.J. Schlesinger. 1990. Replication of togaviridae and flaviviridae, p. 697-710. In B. N. Fields, D. M. Knipe, R.M. Chanock, M.S. Hirsch, J.L. Melnick, T.P. Monath, and B. Roizman (ed.), Virology, 2 ed, vol. 1. Ravens Press, New York.

O'Brien, J., I. Wilson, T. Orton, and F. Pognan. 2000. Investigation of the Alamar Blue (reazurin) fluorescent dye for the assessment of mammalian cell cytotoxicity. Eur J Biochem. 267:5421-5426.

Takhampunya, R., S. Ubol, H. S. Houng, C. E. Cameron, and R. Padmanabhan. 2006. Inhibition of dengue virus replication by mycophenolic acid and ribavirin. J Gen Virol 87:1947-52.

Thein, S., M. M. Aung, T. N. Shwe, M. Aye, A. Zaw, K. Aye, K. M. Aye, and J. Aaskov. 1997. Risk factors in dengue shock syndrome. Am J Trop Med Hyg 56:566-72.

Uchil, P. D., and V. Satchidanandam. 2003. Architecture of the flaviviral replication complex. Protease, nuclease, and detergents reveal encasement within double-layered membrane compartments. J Biol Chem 278:24388-98.

Umareddy, I., A. Chao, A. Sampath, F. Gu, and S. G. Vasudevan. 2006. Dengue virus NS4B interacts with NS3 and dissociates it from single-stranded RNA. J Gen Virol 87:2605-14.

Whitby, K., T. C. Pierson, B. Geiss, K. Lane, M. Engle, Y. Zhou, R. W. Doms, and M. S. Diamond. 2005. Castanospermine, a potent inhibitor of dengue virus infection in vitro and in vivo. J Virol 79:8698-706.

Who. 2002. Dengue and dengue haemorrhagic fever, http://www.who.int/mediacentre/factsheets/fs117/en/.

Who. 1997. Dengue haemorrhagic fever, http://www.who.int/csr/resources/publications/dengue/Denguepublication/en/index.html.

International Search Report and the Written Opinion of PCT/US2009/045921, International Filing Date Jun. 2, 2009, Dated Sep. 1, 2009.

First Examination Report issued in related Indian Appln. Serial No. 8193/DELNP/2010, dated Aug. 19, 2014.

* cited by examiner

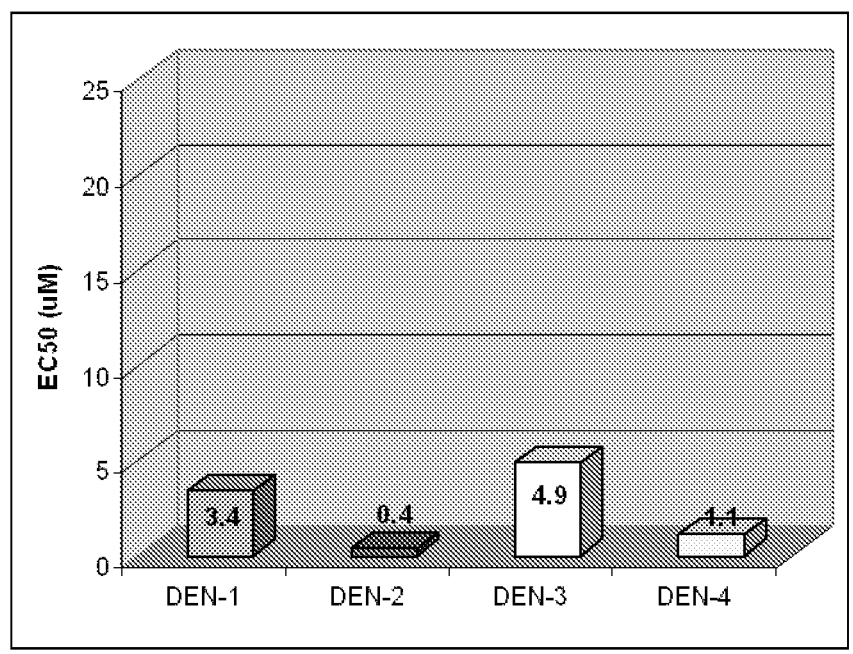

SMALL MOLECULE INHIBITORS FOR THE TREATMENT OR PREVENTION OF DENGUE VIRUS INFECTION

CROSS REFERENCE TO RELATED APPLICATIONS

This application is the United States national phase filing of the corresponding international application number PCT/US2009/045921, filed on Jun. 2, 2009, which claims priority to and benefit of U.S. Application No. 61/058,263, filed Jun. 3, 2008, which applications are hereby incorporated by reference in their entirety.

STATEMENT REGARDING FEDERALLY SPONSORED RESEARCH OR DEVELOPMENT

This invention was made with U.S. government support under Grant No. 1R43AI079937-01A1 awarded by the National Institute of Health (NIH). The U.S. Government has certain rights in the invention.

FIELD OF THE INVENTION

This invention relates to the use of benzoxazole derivatives and analogs, as well as compositions containing the same, for the treatment or prophylaxis of viral diseases associated with the flavivirus family such as Dengue fever, Yellow fever, West Nile, St. Louis encephalitis, Hepatitis C, Murray Valley encephalitis, and Japanese encephalitis.

BACKGROUND OF THE INVENTION

Dengue fever (DF) is an acute febrile disease caused by one of four closely related virus serotypes (DEN-1, DEN-2, DEN-3, and DEN-4). Dengue fever is classified based on its clinical characteristics into classical dengue fever, or the more severe forms, dengue hemorrhagic fever syndrome (DHF), and dengue shock syndrome (DSS). Recovery from infection from one serotype produces life-long immunity to that particular serotype, but provides only short-lived and limited protection against any of the other serotypes (37). Dengue is a member of the Flaviviridae family which are enveloped, positive-sense RNA viruses whose human pathogens also include West Nile virus (WNV), yellow fever virus (YFV), Japanese encephalitis virus (JEV), and tick-borne encephalitis virus (TBEV) among others. Dengue transmission is via the bite of an infected *Aedes aegypti* mosquito which is found in tropical and sub-tropical regions around the world.

Each year regional epidemics of dengue cause significant morbidity and mortality, social disruption and substantial economic burden on the societies affected both in terms of hospitalization and mosquito control. Dengue is considered by the World Health Organization (WHO) to be the most important arthropod-borne viral disease with an estimated 50 million cases of dengue infection, including 500,000 DHF cases and 24,000 deaths worldwide each year (37, 38). WHO estimates that forty percent of the world's population (2.5 billion people) are at risk for DF, DHF, and DSS (37). Dengue is also a NIAID Category A pathogen and in terms of biodefense, represents a significant threat to United States troops overseas. Dengue is an emerging threat to North America with a dramatic increase in severe disease in the past 25 years including major epidemics in Cuba and Venezuela, and outbreaks in Texas and Hawaii (4). Failure to control the mosquito vector and increases in long-distance travel have contributed to the increase and spread of dengue disease. The characteristics of dengue as a viral hemorrhagic fever virus (arthropod-borne, widely spread, and capable of inducing a great amount of cellular damage and eliciting an immune response that can result in severe hemorrhage, shock, and death) makes this virus a unique threat to deployed military personnel around the world as well as to travelers to tropical regions. Preparedness for both biodefense and for the public health challenges posed by dengue will require the development of new vaccines and antiviral therapeutics.

Dengue causes several illnesses with increasing severity being determined in part by prior infection with a different serotype of the virus. Classic dengue fever (DF) begins 3-8 days after the bite of an infected mosquito and is characterized by sudden onset of fever, headache, back pain, joint pain, a measles-like rash, and nausea and vomiting (21). DF is frequently referred to as "breakbone" fever due to these symptoms. The disease usually resolves after two weeks but a prolonged recovery with weakness and depression is common. The more severe form of the disease, dengue hemorrhagic fever (DHF) has a similar onset and early phase of illness as dengue fever. However, shortly after onset the disease is characterized by high fever, enlargement of the liver, and hemorrhagic phenomena such as bleeding from the nose, mouth, and internal organs due to vascular permeability (38). In dengue shock syndrome (DSS) circulatory failure and hypovolaemic shock resulting from plasma leakage occur and can lead to death in 12-24 hours without plasma replacement (38). The case fatality rate of DHF/DSS can be as high as 20% without treatment. DHF has become a leading cause of hospitalization and death among children in many countries with an estimated 500,000 cases requiring hospitalization each year and a case fatality rate of about 5% (37).

The pathogenesis of DHF/DSS is still being studied but is thought to be due in part to an enhancement of virus replication in macrophages by heterotypic antibodies, termed antibody-dependent enhancement (ADE) (8). During a secondary infection, with a different serotype of dengue virus, crossreactive antibodies that are not neutralizing form virusantibody complexes that are taken into monocytes and Langerhans cells (dendritic cells) and increase the number of infected cells (7). This leads to the activation of cytotoxic lymphocytes which can result in plasma leakage and the hemorrhagic features characteristic of DHF and DSS (21). This antibody-dependent enhancement of infection is one reason why the development of a successful vaccine has proven to be so difficult. Although less frequent, DHF/DSS can occur after primary infection (33), so virus virulence (16) and immune activation are also believed to contribute to the pathogenesis of the disease (26).

Dengue is endemic in more than 100 countries in Africa, the Americas, the Eastern Mediterranean, Southeast Asia and the Western Pacific. During epidemics, attack rates can be as high as 80-90% of the susceptible population. All four serotypes of the virus are emerging worldwide, increasing the number of cases of the disease as well as the number of explosive outbreaks. In 2002 for example, there were 1,015, 420 reported cases of dengue in the Americas alone with 14,374 cases of DHF, which is more than three times the number of dengue cases reported in the Americas in 1995 (24).

The dengue genome, approximately 11 kb in length, consists of a linear, single stranded, infectious, positive sense RNA that is translated as a single long polyprotein (reviewed in (29). The genome is composed of seven nonstructural (NS) protein genes and three structural protein genes which encode the nucleocapsid protein (C), a membrane-associated protein (M), and an envelope protein (E). The nonstructural proteins are involved in viral RNA replication (35), viral assembly, and the inflammatory components of the disease (19). The structural proteins are involved mainly in viral particle formation (22). The precursor polyprotein is cleaved by cellular proteinases to separate the structural proteins (18), while a virus-encoded proteinase cleaves the nonstructural region of the polyprotein (6). The genome is capped and does not have a poly(A) tail at the 3' end but instead has a stable stem-loop structure necessary for stability and replication of the genomic RNA (3). The virus binds to cellular receptors via the E protein and undergoes receptor-mediated endocytosis followed by low-pH fusion in lysosomes (20). The viral genome is then uncoated and translated into the viral precursor polyprotein. Co- and posttranslational proteolytic processing separates the structural and nonstructural proteins. The RNA-dependent RNA polymerase along with cofactors synthesizes the minus-strand RNA which serves as a template for the synthesis of the progeny plus-strand RNA (25). Viral replication is membrane associated (1, 34). Following replication, the genome is encapsidated, and the immature virus, surrounded by a lipid envelope buds into the lumen (9). The envelope proteins become glycosylated and mature viruses are released outside the cell. Essential stages or process during the virus life cycle would be possible targets for inhibition from an antiviral drug and include binding of the virus to the cell through the E protein, uptake of the virus into the cell, the capping mechanism, the viral proteinase, the viral RNA-dependent RNA polymerase, and the viral helicase.

Current management of dengue virus-related disease relies solely on vector control. There are no approved antivirals or vaccines for the treatment or prevention of dengue. Ribavirin, a guanosine analogue, has been shown to be effective against a range of RNA virus infections and works against dengue in tissue culture by inhibiting the dengue 2'-O-methyltransferase NS5 domain (2, 10). However, ribavirin did not show protection against dengue in a mouse model (15) or a rhesus monkey model (17), instead it induced anemia and thrombocytosis. While there are no currently available approved vaccines, multivalent dengue vaccines have shown some limited potential in humans (5, 12, 13, 28). However, vaccine development is difficult due to the presence of four distinct serotypes of the virus which each cause disease. Vaccine development also faces the challenge of ADE where unequal protection against the different strains of the virus could actually increase the risk of more serious disease. Therefore there is a need for antiviral drugs that target all of the serotypes of dengue. An antiviral drug administered early during dengue infection that inhibits viral replication would prevent the high viral load associated with DHF and be an attractive strategy in the treatment and prevention of disease. An antiviral drug that inhibits viral replication could be administered prior to travel to a dengue endemic region to prevent acquisition of disease, or for those that have previously been exposed to dengue, could prevent infection by another serotype of virus and decrease the chance of life-threatening DHF and DSS. Having an antiviral drug would also aid vaccine development by having a tool at hand to treat complications that may arise due to unequal immune protection against the different serotypes. Although a successful vaccine could be a critical component of an effective biodefense, the typical delay to onset of immunity, potential side-effects, cost, and logistics associated with large-scale civilian vaccinations against a low-threat risk agent suggest that a comprehensive biodefense include a separate rapid-response element. Thus, there remains an urgent need to develop a safe and effective product to protect against flavivirus infection.

BRIEF DESCRIPTION OF THE DRAWINGS

FIG. 1 shows the effective concentration (μM) of compound 3 against each serotype of dengue virus as determined by yield assay in vero cells.

SUMMARY OF THE INVENTION

The present invention provides a pharmaceutical composition comprising a pharmaceutically acceptable carrier and a compound having the following general Formula I or a pharmaceutically acceptable salt thereof:

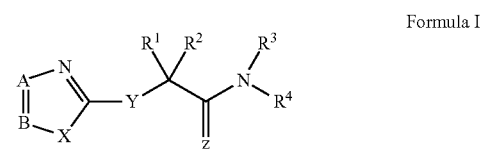

Formula I wherein A is N or C—$R^5$ and B is N or C—$R^6$, wherein $R^5$ and $R^6$ are independently selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano, and nitro, or optionally $R^5$ and $R^6$ together with the carbons they are attached to form a substituted or unsubstituted ring, which may be aromatic or non-aromatic and optionally includes one or more heteroatoms in the ring and is optionally is fused with an aromatic or aliphatic ring;

X, Y and Z are independently selected from the group consisting of O, S and N—R', wherein $R^2$ is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl, and substituted carbamoyl;

$R^1$ and $R^2$ are independently selected from the group consisting of hydrogen, substituted or unsubstituted alkyl, alkenyl, alkynyl, cycloalkyl, heterocycloalkyl, arylalkyl, aryl, heteroaryl, alkyloxy, aryloxy, heteroaryloxy, acyloxy, arylacyloxy, heteroarylacyloxy, alkylsulfonyloxy, arylsulfonyloxy, alkylthio, arylthio, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, cyano, isocyano, and nitro, or optionally $R^1$ and $R^2$ together with the carbon they are attached to may form a substituted or unsubstituted ring, which optionally includes one or more heteroatoms in the ring and optionally is fused with an aromatic or aliphatic ring;

$R^3$ and $R^4$ are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl, and substituted carbamoyl, or optionally $R^3$ and $R^4$ together with the nitrogen atom they are attached to form a substituted or unsubstituted ring, which optionally includes one or more heteroatoms in the ring and optionally is fused with an aromatic or aliphatic ring; and $R^1$ or $R^2$ and $R^3$ or $R^4$ together with the carbon or nitrogen they are attached to and the carbon that Z is attached to optionally form a substituted or unsubstituted ring, which optionally includes one or more heteroatoms in the ring.

The present invention further provides a method for the treatment or prophylaxis of a viral infection or disease associated therewith, comprising administering in a therapeutically effective amount to a mammal in need thereof, a compound of Formula I below or a pharmaceutically acceptable salt thereof:

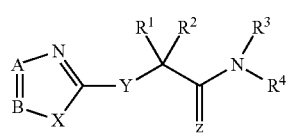

Formula I wherein A is N or C—$R^5$ and B is N or C—$R^6$, wherein $R^5$ and $R^6$ are independently selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano, and nitro, or optionally $R^5$ and $R^6$ together with the carbons they are attached to form a substituted or unsubstituted ring, which may be aromatic or non-aromatic and optionally includes one or more heteroatoms in the ring and is optionally is fused with an aromatic or aliphatic ring; X, Y and Z are independently selected from the group consisting of O, S and N—R', wherein $R^2$ is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl, and substituted carbamoyl;

$R^1$ and $R^2$ are independently selected from the group consisting of hydrogen, substituted or unsubstituted alkyl, alkenyl, alkynyl, cycloalkyl, heterocycloalkyl, arylalkyl, aryl, heteroaryl, alkyloxy, aryloxy, heteroaryloxy, acyloxy, arylacyloxy, heteroarylacyloxy, alkylsulfonyloxy, arylsulfonyloxy, alkylthio, arylthio, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, cyano, isocyano, and nitro, or optionally $R^1$ and $R^2$ together with the carbon they are attached to may form a substituted or unsubstituted ring, which optionally includes one or more heteroatoms in the ring and optionally is fused with an aromatic or aliphatic ring;

$R^3$ and $R^4$ are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl, and substituted carbamoyl, or optionally $R^3$ and $R^4$ together with the nitrogen atom they are attached to form a substituted or unsubstituted ring, which optionally includes one or more heteroatoms in the ring and optionally is fused with an aromatic or aliphatic ring; and $R^1$ or $R^2$ and $R^3$ or $R^4$ together with the carbon or nitrogen they are attached to and the carbon that Z is attached to optionally form a substituted or unsubstituted ring, which optionally includes one or more heteroatoms in the ring.

Other objects and advantages of the present invention will become apparent from the following description and appended claims.

DETAILED DESCRIPTION OF THE INVENTION

The compounds of the invention are of the following general Formula I:

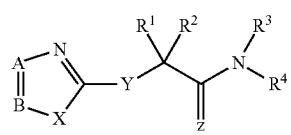

Formula I wherein A is N or C—$R^5$ and B is N or C—$R^6$, wherein $R^5$ and $R^6$ are independently selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano, and nitro, or optionally $R^5$ and $R^6$ together with the carbons they are attached to form a substituted or unsubstituted ring, which may be aromatic or non-aromatic and optionally includes one or more heteroatoms in the ring and is optionally is fused with an aromatic or aliphatic ring;

X, Y and Z are independently selected from the group consisting of O, S and N—$R^7$, wherein $R^7$ is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl, and substituted carbamoyl;

$R^1$ and $R^2$ are independently selected from the group consisting of hydrogen, substituted or unsubstituted alkyl, alkenyl, alkynyl, cycloalkyl, heterocycloalkyl, arylalkyl, aryl, heteroaryl, alkyloxy, aryloxy, heteroaryloxy, acyloxy, arylacyloxy, heteroarylacyloxy, alkylsulfonyloxy, arylsulfonyloxy, alkylthio, arylthio, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, cyano, isocyano, and nitro, or optionally $R^1$ and $R^2$ together with the carbon they are attached to may form a substituted or unsubstituted ring, which optionally includes one or more heteroatoms in the ring and optionally is fused with an aromatic or aliphatic ring;

$R^3$ and $R^4$ are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl, and substituted carbamoyl, or optionally $R^3$ and $R^4$ together with the nitrogen atom they are attached to form a substituted or unsubstituted ring, which optionally includes one or more heteroatoms in the ring and optionally is fused with an aromatic or aliphatic ring; and $R^1$ or $R^2$ and $R^3$ or $R^4$ together with the carbon or nitrogen they are attached to and the carbon that Z is attached to optionally form a substituted or unsubstituted ring, which optionally includes one or more heteroatoms in the ring.

Preferably, each of $R^1$ and $R^2$ is hydrogen. Also preferably, Y is S, Z is O. Again preferably, $R^3$ and $R^4$ together with the nitrogen atom they are attached to form a substituted ring.

Preferably, the compound of the present invention is selected from the group consisting of: N-[2-(2-Morpholin-4-yl-2-oxo-ethylsulfanyl)-benzothiazol-6-yl]-3-phenyl-propionamide; N-[2-(2-oxo-2-piperidin-1-yl-ethylsulfanyl)-benzothiazol-6-yl]-propionamide; 1'-[2-(Benzooxazol-2-ylsulfanyl)-acetyl]-[1,4']bipiperidinyl-4'-carboxylic acid amide; 3-(Benzothiazol-2-ylsulfanyl)-1-benzyl-pyrrolidine-2,5-dione; 2-Methyl-N-[2-(2-morpholin-4-yl-2-oxo-ethylsulfanyl)-benzothiazol-6-yl]-benzamide; 2,4-Dichloro-N-[2-(2-morpholin-4-yl-2-oxo-ethylsulfanyl)-benzothiazol-6-yl]-benzamide; 1-(3,4-Dihydro-1H-isoquinolin-2-yl)-2-(6-ethoxy-benzothiazol-2-ylsulfanyl)-ethanone; 2-(1H-Benzoimidazol-2-ylsulfanyl)-1-[4-(4-fluoro-phenyl)-piperazin-1-yl]-ethanone; 1'-[2-(Benzothiazol-2-ylsulfanyl)-acetyl]-[1,4']bipiperidinyl-4'-carboxylic acid amide; 2-(6-Amino-benzothiazol-2-ylsulfanyl)-1-(4-benzyl-piperazin-1-yl)-ethanone; 2-(Benzooxazol-2-ylsulfanyl)-1-(4-benzyl-piperazin-1-yl)-ethanone; 1-[3-(2-Methoxy-benzoyl)-piperidin-1-yl]-2-(5-methyl-1H-benzoimidazol-2-ylsulfanyl)-ethanone; 3-Methyl-N-[2-(2-morpholin-4-yl-2-oxo-ethylsulfanyl)-benzothiazol-6-yl]-benzamide; 2-(6-Ethoxy-benzothiazol-2-ylsulfanyl)-1-(4-phenyl-piperazin-1-yl)-ethanone; 2-Diethylcarbamoylmethylsulfanyl-benzoimidazole-1-carboxylic acid cyclohexylamide; 2-(6-Amino-benzothiazol-2-ylsulfanyl)-1-morpholin-4-yl-ethanone; 2-(6-{[1-(4-Bromo-phenyl)-meth-(E)-ylidene]-amino}-benzothiazol-2-ylsulfanyl)-1-morpholin-4-yl-ethanone; 2-(6-{[1-(4-Chloro-phenyl)-meth-(E)-ylidene]-amino}-benzothiazol-2-ylsulfanyl)-1-morpholin-4-yl-ethanone; 2-(6-{[1-Anthracen-9-yl-meth-(E)-ylidene]-amino}-benzothiazol-2-ylsulfanyl)-1-morpholin-4-yl-ethanone; 2-Bromo-N-[2-(2-morpholin-4-yl-2-oxo-ethylsulfanyl)-benzothiazol-6-yl]-benzamide; N-[2-(2-Morpholin-4-yl-2-oxo-ethylsulfanyl)-benzothiazol-6-yl]-benzamide; 4-Butoxy-N-[2-(2-morpholin-4-yl-2-oxo-ethylsulfanyl)-benzothiazol-6-yl]-benzamide; 1-Morpholin-4-yl-2-(6-{[1-[5-(1-phenyl-1H-tetrazol-5-ylsulfanyl)-furan-2-yl]-meth-(E)-ylidene]-amino}-benzothiazol-2-ylsulfanyl)-ethanone; 2-(6-{[1-(2,6-Dichloro-phenyl)-meth-(E)-ylidene]-amino}-benzothiazol-2-ylsulfanyl)-1-morpholin-4-yl-ethanone; 2-(6-{[1-(4-Iodo-phenyl)-meth-(E)-ylidene]-amino}-benzothiazol-2-ylsulfanyl)-1-morpholin-4-yl-ethanone; 2-(6-{[1-(4-Fluoro-phenyl)-meth-(E)-ylidene]-amino}-benzothiazol-2-ylsulfanyl)-1-morpholin-4-yl-ethanone; 2-Fluoro-N-[2-(2-morpholin-4-yl-2-oxo-ethylsulfanyl)-benzothiazol-6-yl]-benzamide; 2-Methoxy-N-[2-(2-morpholin-4-yl-2-oxo-ethylsulfanyl)-benzothiazol-6-yl]-benzamide; 3,4-Dichloro-N-[2-(2-morpholin-4-yl-2-oxo-ethylsulfanyl)-benzothiazol-6-yl]-benzamide; 2-[6-(1,3-Dioxo-1,3-dihydro-isoindol-2-yl)-benzothiazol-2-ylsulfanyl]-N,N-diethyl-acetamide; 2-(6-Amino-benzothiazol-2-ylsulfanyl)-N-[2-(2-morpholin-4-yl-2-oxo-ethylsulfanyl)-benzothiazol-6-yl]-acetamide; Cyclohexanecarboxylic acid [2-(2-morpholin-4-yl-2-oxo-ethylsulfanyl)-benzothiazol-6-yl]-amide; 2-(1-Methyl-1H-imidazol-2-ylsulfanyl)-N-[2-(2-morpholin-4-yl-2-oxo-ethylsulfanyl)-benzothiazol-6-yl]-acetamide; 2-(Benzothiazol-2-ylsulfanyl)-N-[2-(2-morpholin-4-yl-2-oxo-ethylsulfanyl)-benzothiazol-6-yl]-acetamide; 2-(4,5-Diphenyl-4H-[1,2,4]triazol-3-ylsulfanyl)-N-[2-(2-morpholin-4-yl-2-oxo-ethylsulfanyl)-benzothiazol-6-yl]-acetamide; 2-(4-Methyl-5-naphthalen-1-ylmethyl-4H-[1,2,4]triazol-3-ylsulfanyl)-N-[2-(2-morpholin-4-yl-2-oxo-ethylsulfanyl)-benzothiazol-6-yl]-acetamide; 2-(4-Methyl-5-phenyl-4H-[1,2,4]triazol-3-ylsulfanyl)-N-[2-(2-morpholin-4-yl-2-oxo-ethylsulfanyl)-benzothiazol-6-yl]-acetamide; N-[2-(2-Morpholin-4-yl-2-oxo-ethylsulfanyl)-benzothiazol-6-yl]-2-naphthalen-1-yl-acetamide; 1-(4-Benzothiazol-2-yl-piperazin-1-yl)-2-(6-ethoxy-benzothiazol-2-ylsulfanyl)-ethanone; 2-(6-Amino-benzothiazol-2-ylsulfanyl)-1-(4-benzothiazol-2-yl-piperazin-1-yl)-ethanone; 2-(Benzothiazol-2-ylsulfanyl)-1-piperidin-1-yl-ethanone; 2-(1H-Benzoimidazol-2-ylsulfanyl)-1-morpholin-4-yl-ethanone; 1-Azepan-1-yl-2-(1H-benzoimidazol-2-ylsulfanyl)-ethanone; 2-(1H-Benzoimidazol-2-ylsulfanyl)-1-(4-methyl-piperidin-1-yl)-ethanone; 2-(1H-Benzoimidazol-2-ylsulfanyl)-1-pyrrolidin-1-yl-ethanone; 2-(1H-Benzoimidazol-2-ylsulfanyl)-1-(4-phenyl-piperazin-1-yl)-ethanone; 2-(Benzooxazol-2-ylsulfanyl)-1-(3,4-dihydro-1H-isoquinolin-2-yl)-ethanone; 2-(2-oxo-2-piperidin-1-yl-ethylsulfanyl)-benzooxazole-5-carboxylic acid; 2-(6-Nitro-benzothiazol-2-ylsulfanyl)-1-piperidin-1-yl-ethanone; 1-(4-Benzothiazol-2-yl-piperazin-1-yl)-2-(benzothiazol-2-ylsulfanyl)-ethanone; 2-(1-Phenyl-1H-benzoimidazol-2-ylsulfanyl)-1-(4-phenyl-piperazin-1-yl)-ethanone; 2-(6-Nitro-benzothiazol-2-ylsulfanyl)-1-(4-phenyl-piperazin-1-yl)-ethanone; 2-[5-(Benzothiazol-2-ylsulfanylmethyl)-[1,3,4]oxadiazol-2-ylsulfanyl]-N-cyclohexyl-acetamide; N-{2-[2-oxo-2-(4-phenyl-piperazin-1-yl)-ethylsulfanyl]-benzothiazol-6-yl}-propionamide; 2-(6-Nitro-benzothiazol-2-ylsulfanyl)-1-pyrrolidin-1-yl-ethanone; 4-Methyl-N-[2-(2-oxo-2-piperidin-1-ylethylsulfanyl)-benzothiazol-6-yl]-benzamide; N-{2-[2-Oxo-2-(4-phenyl-piperazin-1-yl)-ethylsulfanyl]-benzothiazol-6-yl}-acetamide; 4-Chloro-N-[2-(2-oxo-2-pyrrolidin-1-yl-ethylsulfanyl)-benzothiazol-6-yl]-benzamide; 2-(6-Amino-benzothiazol-2-ylsulfanyl)-1-pyrrolidin-1-yl-ethanone; 3-(4-Benzothiazol-2-yl-piperazin-1-yl)-1-(4-fluoro-phenyl)-pyrrolidine-2,5-dione; 2-(1H-Benzoimidazol-2-ylsulfanyl)-1-(3,4-dihydro-1H-isoquinolin-2-yl)-ethanone; N,N-Diethyl-2-(5-methyl-1H-benzoimidazol-2-ylsulfanyl)-acetamide; 2-(Benzothiazol-2-ylsulfanyl)-1-pyrrolidin-1-yl-ethanone; 3,4-Dimethoxy-N-[2-(2-morpholin-4-yl-2-oxo-ethylsulfanyl)-benzothiazol-6-yl]-benzamide; 2-Bromo-N-[2-(2-oxo-2-pyrrolidin-1-yl-ethylsulfanyl)-benzothiazol-6-yl]-benzamide; 1-[2-(Benzothiazol-2-ylsulfanyl)-acetyl]-piperidine-4-carboxylic acid amide; 1-[2-(Benzooxazol-2-ylsulfanyl)-acetyl]-piperidine-4-carboxylic acid amide; 1-[2-(1H-Benzoimidazol-2-ylsulfanyl)-acetyl]-piperidine-4-carboxylic acid amide; 1'-[2-(4-Ethyl-5-phenyl-4H-[1,2,4]triazol-3-ylsulfanyl)-acetyl]-[1,4']bipiperidinyl-4'-carboxylic acid amide; 1'-[2-(1H-Benzoimidazol-2-ylsulfanyl)-acetyl]-[1,4']bipiperidinyl-4'-carboxylic acid amide; 2-(Benzothiazol-2-ylsulfanyl)-1-[4-(4-fluoro-phenyl)-piperazin-1-yl]-ethanone; 1-(4-Benzhydryl-piperazin-1-yl)-2-(benzothiazol-2-ylsulfanyl)-ethanone; 1-[4-(3-Chloro-phenyl)-piperazin-1-yl]-2-(6-nitro-benzothiazol-2-ylsulfanyl)-ethanone; 2-(5-Chloro-benzooxazol-2-ylsulfanyl)-1-morpholin-4-yl-ethanone; N-{2-[2-oxo-2-(4-phenyl-piperazin-1-yl)-ethylsulfanyl]-benzothiazol-6-yl}-butyramide; 2-(Benzooxazol-2-ylsulfanyl)-1-(4-phenyl-piperazin-1-yl)-ethanone; 2-(6-Amino-benzothiazol-2-ylsulfanyl)-1-[4-(4-chloro-phenyl)-piperazin-1-yl]-ethanone; 2-(Benzooxazol-2-ylsulfanyl)-1-[4-(4-p-tolyl-phthalazin-1-yl)-piperazin-1-yl]-ethanone; 2-{1-[(2,6-Dimethyl-phenylcarbamoyl)-methyl]-1H-benzoimidazol-2-ylsulfanyl}-acetamide; 2-(Benzooxazol-2-ylsulfanyl)-1-[4-(4-chloro-phenyl)-piperazin-1-yl]-ethanone; 1-(3,4-Dihydro-1H-isoquinolin-2-yl)-2-(1-methyl-1H-benzoimidazol-2-ylsulfanyl)-ethanone; and 2-(1-Benzenesulfonyl-1H-benzoimidazol-2-ylsulfanyl)-1-pyrrolidin-1-yl-ethanone.

Most preferably, the compound of the present invention is 1'-[2-(Benzooxazol-2-ylsulfanyl)-acetyl]-[1,4']bipiperidinyl-4T-carboxylic acid amide.

The method of the present invention is for the treatment or prophylaxis of a viral infection or disease associated therewith, comprising administering in a therapeutically effective amount to a mammal in need thereof, a compound of Formula I described above.

Preferably, the mammal is a human and the viral infection is a flavivirus infection. More preferably, the flavivirus virus is selected from the group consisting of Dengue virus, West Nile virus, yellow fever virus, Japanese encephalitis virus, and tick-borne encephalitis virus. Most preferably, the flavivirus is a Dengue virus selected from the group consisting of DEN-1, DEN-2, DEN-3, and DEN-4.

Preferably, the viral infection is associated with a condition selected from the group consisting of Dengue fever, Yellow fever, West Nile, St. Louis encephalitis, Hepatitis C, Murray Valley encephalitis, and Japanese encephalitis. Most preferably, the viral infection is associated with Dengue fever wherein said Dengue fever is selected from the group consisting of classical dengue fever, dengue hemorrhagic fever syndrome, and dengue shock syndrome.

The method of the present invention may also comprise co-administration of: a) other antivirals such as Ribavirin or cidofovir; b) vaccines; and/or c) interferons or pegylated interferons.

Definitions

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, experimental animals including rats, mice, and guinea pigs, domestic and farm animals, and zoo, sports, or pet animals, such as dogs, horses, cats, cows, and the like.

The term "efficacy" as used herein refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkylamino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Amino" refers to the group —$NH_2$.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one, and the like) provided that the point of attachment is through an aromatic ring atom.

"Substituted aryl" refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OS(O)_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2NRR$ where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Halo" or "halogen" refers to fluoro, chloro, bromo and iodo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (=O). The term "heteroaryl having two nitrogen atoms in the heteroaryl, ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substiruted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Sulfonyl" refers to the group —S(O)$_2$R where R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable.

Pharmaceutically-acceptable salts refer to pharmaceutically-acceptable salts of the compounds, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Pro-drugs are prepared by modifying functional groups present in such a way that the modifications may be cleaved in vivo to release the parent compound. Pro-drugs include compounds wherein a hydroxy, amino, or sulfhydryl group is bonded to any group that may be cleaved in vivo to regenerate the free hydroxyl, amino, or sulfhydryl group, respectively. Examples of pro-drugs include, but are not limited to esters (e.g., acetate, formate, and benzoate derivatives), carbamates (e.g., N,N-dimethylamino-carbonyl) of hydroxy functional groups, and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically-effective amount" means the amount of a compound that, when administered to a mammal for treating a disease, is sufficient to effect such treatment for the disease. The "therapeutically-effective amount" will vary depending on the compound, the disease, and its severity and the age, weight, etc., of the mammal to be treated.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is able to maintain a formulation pH in the range of 4 to 8. Generally, a 1:1 to 10:1 mole ratio of buffer (where the moles of buffer are taken as the combined moles of the buffer ingredients, e.g., sodium citrate and citric acid) to drug is used.

A useful buffer is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the compounds, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly (vinyl alcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host.

Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

In the examples below, if an abbreviation is not defined above, it has its generally accepted meaning. Further, all temperatures are in degrees Celsius (unless otherwise indicated). The following Methods were used to prepare the compounds set forth below as indicated.

EXAMPLE 1

Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

EXAMPLE 2

Formulation 2

A tablet formula is prepared using the ingredients below:

| Ingredient | Quantity (mg/capsule) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

EXAMPLE 3

Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

EXAMPLE 4

Formulation 4

Tablets, each containing 30 mg of active ingredient, are prepared as follows:

| Ingredient | Quantity (mg/capsule) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

EXAMPLE 5

Formulation 5

Capsules, each containing 40 mg of medicament, are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

EXAMPLE 6

Formulation 6

Suppositories, each containing 25 mg of active ingredient, are made as follows:

| Ingredient | Amount |
|---|---|
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 7

Formulation 7

Suspensions, each containing 50 mg of medicament per 5.0 ml dose, are made as follows:

| Ingredient | Amount |
|---|---|
| Active Ingredient | 50.0 mg |
| Xanthan gum | 4.0 mg |
| Sodium carboxymethyl cellose (11%) Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a NO. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 8

Formulation 8

Hard gelatin tablets, each containing 15 mg of active ingredient, are made as follows:

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

EXAMPLE 9

Formulation 9

An intravenous formulation may be prepared as follows:

| Ingredient | (mg/capsule) |
|---|---|
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

EXAMPLE 10

Formulation 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

EXAMPLE 11

Formulation 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final Concentration |
| --- | --- | --- |
| Sodium Bicarbonate | 0.5 g | 0.5% |
| Saline | q.s. ad 100.0 ml | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/100.0 mL | Final Concentration |
| --- | --- | --- |
| Candidate Compound | 0.300 g | 30.0 mg/mL |
| .05% Sodium Bicarbonate/Saline Stock Solution | q.s. ad 10.0 mL | q.s. ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix.

EXAMPLE 12

Development of a High-Throughput Screening for Measurement of Dengue Virus-Induced Cytopathic Effect A sensitive and reproducible high-throughput screening (HTS) assay has been established to measure dengue virus-induced cytopathic effect (CPE). To determine the amount of dengue virus stock required to produce complete CPE in 5 days, Vero cell monolayers were seeded on 96-well plates and infected with 10-fold serial dilutions of the dengue virus stock representing a multiplicity of infection (MOI) of approximately 0.001 PFU/cell to 0.1 PFU/cell. At 5 days post-infection, the cultures were fixed with 5% glutaraldehyde and stained with 0.1% crystal violet. Virus-induced CPE was quantified spectrophotometrically at $OD_{570}$. From this analysis, an MOI of 0.1 PFU/cell of dengue virus stock was chosen for use in the HTS assay. To establish the signal-to-noise ratio (S/N) of the 96-well assay and evaluate the well-to-well and assay-to-assay variability, five independent experiments were performed. Vero cell monolayers were infected with 0.1 PFU/cell of dengue virus stock. Each plate contained the following controls: quadruplicate virus-infected wells, quadruplicate uninfected cell wells and a dose response curve in duplicate for ribavirin at 500, 250, 125 and 62 µM, as reference standards. At day 5 post-infection, the plates were processed as described above.

The dengue virus CPE assay was used to evaluate compounds from a chemical library for those that inhibit dengue virus-induced CPE. Each evaluation run consisted of 48 96-well plates with 80 compounds per plate to generate 4,608 data points per run. At this throughput we are capable of evaluating 200,000 compounds in about 52 weeks. Compounds were dissolved in DMSO and diluted in medium such that the final concentration in each well was 5 µM compound and 0.5% DMSO. The compounds were added robotically to the culture medium using the PerkinElmer MultiPROBE® II HT PLUS robotic system. Following compound addition, cultures were infected with dengue virus (DEN-2 strain New Guinea C). After 5 days incubation, plates were processed and CPE quantified on a PerkinElmer EnVision II plate reader system.

The results of these experiments indicated that the 96-well assay format is robust and reproducible. The S/N ratio (ratio of signal of cell control wells (signal) to virus control wells (noise)) was 5.0±1.2. The well-to-well variability was determined for each individual plate and found to have a coefficient of variance of less than 10% for both positive control and negative control wells, and overall assay-to-assay variability was less than 15%. Using this assay, the $EC_{50}$ values for ribavirin were determined to be 125±25 µM, respectively. The effectiveness of ribavirin against dengue varies with the cell type used, but the values we obtained were within the range of published values for this compound (2, 14, 32). Taken together, these results show that a sensitive and reproducible HTS assay has been successfully developed to evaluate our compound library for inhibitors of dengue virus replication.

EXAMPLE 13

Determining Anti Dengue-2 Activity of Compounds of the Invention

The assay described in Example 12 was the basis of a high-throughput screen for dengue virus inhibitors, against which a library of 210,000 compounds was tested. Compounds that inhibited dengue virus induced CPE by at least 50% were further investigated for chemical tractability, potency, and selectivity.

Initially, the chemical structures of the hit compounds were examined for chemical tractability. A chemically tractable compound is defined as one that is synthetically accessible using reasonable chemical methodology, and which possesses chemically stable functionalities and potential drug-like qualities. Hits that passed this medicinal chemistry filter were evaluated for their potency. Compound potency was determined by evaluating inhibitory activity across a broad range of concentrations. Nonlinear regression was used to generate best-fit inhibition curves and to calculate the 50% effective concentration ($EC_{50}$). The selectivity or specificity of a given compound is typically expressed as a ratio of its cytotoxicity to its biological effect. A cell proliferation assay is used to calculate a 50% cytotoxicity concentration ($CC_{50}$); the ratio of this value to the $EC_{50}$ is referred to as the therapeutic index (T.I.=$CC_{50}/EC_{50}$). Two types of assays have been used to determine cytotoxicity, both of which are standard methods for quantitating the reductase activity produced in metabolically active cells (30). One is a colorimetric method that measures the reduction of 3-(4,5-dimethylthiazol-2-yl)-2,5-diphenyl-tetrazolium bromide (MTT), and the other uses fluorimetry to measure the reduction of resazurin (Alamar Blue). Selectivity could be further characterized by assessing the inhibitory action against viruses from unrelated virus families. Twenty-two quality dengue hits were discovered in the pool of initial hits from the HTS screening, all with $EC_{50}$ values below 25 μM. Verification that these compounds act against each of the four serotypes of dengue was done with yield assays carried out at several drug concentrations, and the titer determined for each.

Compounds that were active in the primary screen were tested for activity in viral yield assays. Table 1 shows some of the compounds that were tested for activity against Dengue-2 (Strain New Guinea C) in a viral yield assay at a range of concentrations. Vero cells in 12-well plates were infected with dengue-2 virus at a multiplicity of infection (MOI) of 0.1, treated with compound (or DMSO as a control), incubated at 37° C., harvested 48 hours post infection and titered on Vero cells as described above. The EC50 was calculated through ExcelFit. Those compounds with activity below 1 μM are indicated with "A", those with activity between 1 and 10 μM are indicated with "B", and those with activity between 10 and 25 μM with "C".

Compound 3 was identified as one of the most potent and selective compounds from within the pool of the initial 22 quality hits, with activity against all four serotypes of dengue (FIG. 1). Chemical analogs of this compound were obtained from commercial vendors, and these analogs were tested as described in order to define the relationship between chemical structure and biological activity (see Table 1).

TABLE 1

List of compounds of the present invention and their anti-dengue 2 viral activity

| Compound | Chemical Structure | Molecular Weight | Chemical Name | Activity  A: $EC_{50} \leq$ 1 uM;  B: 1 < $EC_{50} \leq$ 10 uM;  C: 10 < $EC_{50} \leq$ 25 uM;  D: $EC_{50} >$ 25 uM;  n/a: Not determined |
|---|---|---|---|---|
| 1 | 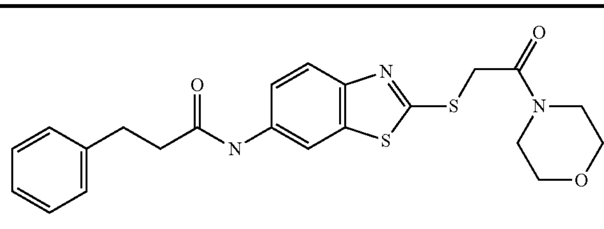 | 441.6 | N-[2-(2-Morpholin-4-yl-2-oxo-ethylsulfanyl)-benzothiazol-6-yl)-3-phenyl-propionamide | A |
| 2 | 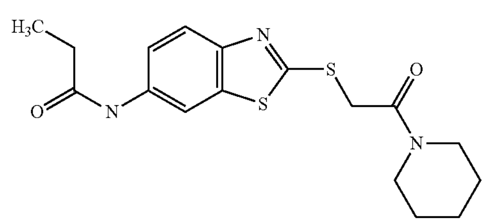 [SMILES: CCC(=O)Nc1ccc2nc(SCC(=O)N3CCCCC3)sc2c1] | 363.5 | N-[2-(2-Oxo-2-piperidin-1-yl-ethylsulfanyl)-benzothiazol-6-yl]-propionamide | A |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 3 | 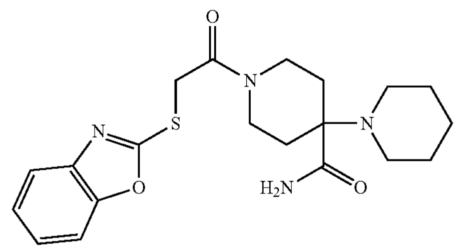 [SMILES: NC(=O)C1(N2CCCCC2)CCN(C(=O)CSc2nc3ccccc3o2)CC1] | 402.5 | 1'-[2-(Benzooxazol-2-ylsulfanyl)-acetyl]-[1,4']bipiperidinyl-4'-carboxylic acid amide | A |
| 4 | 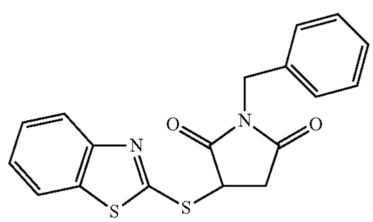 [SMILES: O=C1CC(Sc2nc3ccccc3s2)C(=O)N1Cc1ccccc1] | 354.5 | 3-(Benzothiazol-2-ylsulfanyl)-1-benzyl-pyrrolidine-2,5-dione | A (toxic) |
| 5 | 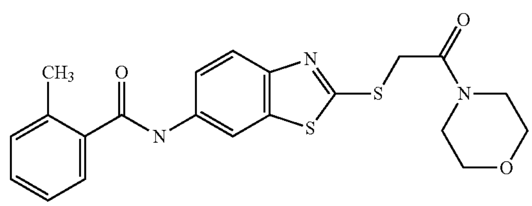 | 427.5 | 2-Methyl-N-[2-(2-morpholin-4-yl-2-oxo-ethylsulfanyl)-benzothiazol-6-yl]-benzamide | B |
| 6 | 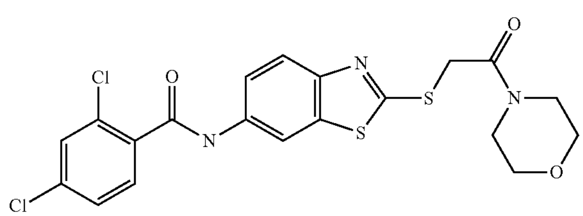 [SMILES: O=C(Nc1ccc2nc(SCC(=O)N3CCOCC3)sc2c1)c1ccc(Cl)cc1Cl] | 482.4 | 2,4-Dichloro-N-[2-(2-morpholin-4-yl-2-oxo-ethylsulfanyl)-benzothiazol-6-yl]-benzamide | B |
| 7 | 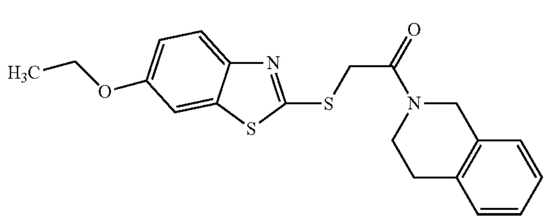 [SMILES: CCOc1ccc2nc(SCC(=O)N3CCc4ccccc4C3)sc2c1] | 384.5 | 1-(3,4-Dihydro-1H-isoquinolin-2-yl)-2-(6-ethoxy-benzothiazol-2-ylsulfanyl)-ethanone | B |

TABLE 1-continued

List of compounds of the present invention and their anti-dengue 2 viral activity

| Compound | Chemical Structure | Molecular Weight | Chemical Name | Activity A: $EC_{50} \leq 1$ uM; B: $1 < EC_{50} \leq 10$ uM; C: $10 < EC_{50} \leq 25$ uM; D: $EC_{50} > 25$ uM; n/a: Not determined |
|---|---|---|---|---|
| 8 | 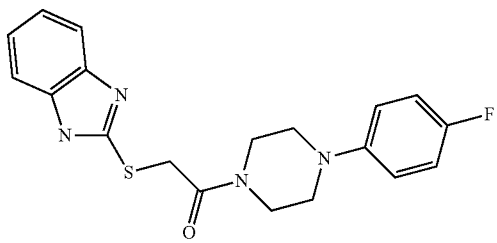 [SMILES: O=C(CSc1nc2ccccc2[nH]1)N1CCN(c2ccc(F)cc2)CC1] | 370.5 | 2-(1H-Benzoimidazol-2-ylsulfanyl)-1-[4-(4-fluorophenyl)-piperazin-1-yl]-ethanone | B |
| 9 | 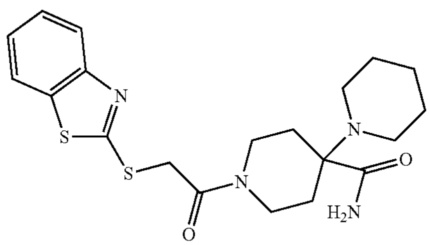 [SMILES: NC(=O)C1(N2CCCCC2)CCN(C(=O)CSc2nc3ccccc3s2)CC1] | 418.6 | 1'-[2-(Benzothiazol-2-ylsulfanyl)-acetyl]-[1,4']bipiperidinyl-4'-carboxylic acid amide | B |
| 10 | 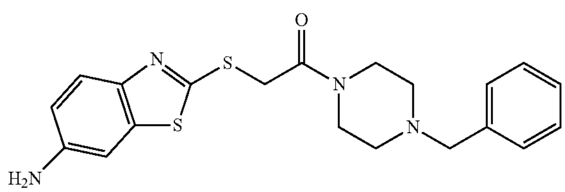 [SMILES: Nc1ccc2nc(SCC(=O)N3CCN(Cc4ccccc4)CC3)sc2c1] | 398.6 | 2-(6-Amino-benzothiazol-2-ylsulfanyl)-1-(4-benzyl-piperazin-1-yl)-ethanone | B |
| 11 | 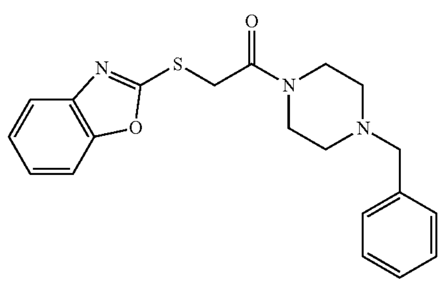 [SMILES: O=C(CSc1nc2ccccc2o1)N1CCN(Cc2ccccc2)CC1] | 367.5 | 2-(Benzooxazol-2-ylsulfanyl)-1-(4-benzyl-piperazin-1-yl)-ethanone | B |
| 12 | 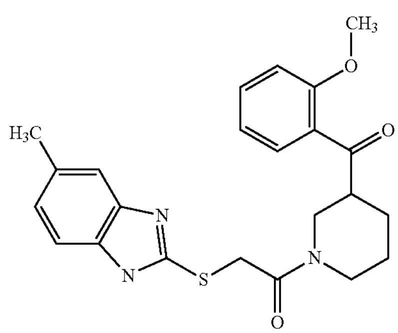 [SMILES: COc1ccccc1C(=O)C1CCCN(C(=O)CSc2nc3cc(C)ccc3[nH]2)C1] | 423.5 | 1-[3-(2-Methoxy-benzoyl)-piperidin-1-yl]-2-(5-methyl-1H-benzoimidazol-2-ylsulfanyl)-ethanone | B (toxic) |

TABLE 1-continued

List of compounds of the present invention and their anti-dengue 2 viral activity

| Compound | Chemical Structure | Molecular Weight | Chemical Name | Activity<br>A: $EC_{50} \leq$ 1 uM;<br>B: $1 < EC_{50} \leq$ 10 uM;<br>C: $10 < EC_{50} \leq$ 25 uM;<br>D: $EC_{50} >$ 25 uM;<br>n/a: Not determined |
|---|---|---|---|---|
| 13 | 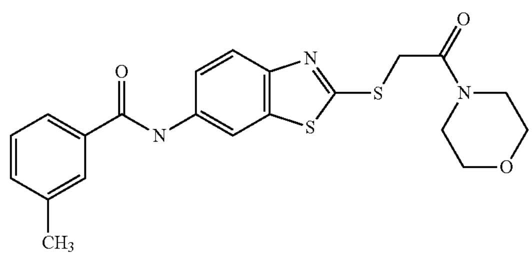 [SMILES: Cc1cccc(C(=O)Nc2ccc3nc(SCC(=O)N4CCOCC4)sc3c2)c1] | 427.5 | 3-Methyl-N-[2-(2-morpholin-4-yl-2-oxo-ethylsulfanyl)-benzothiazol-6-yl]-benzamide | C |
| 14 | 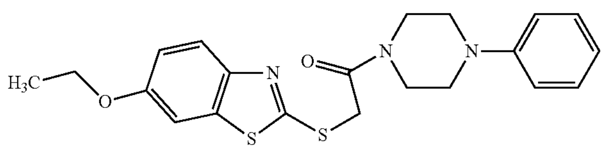 [SMILES: CCOc1ccc2nc(SCC(=O)N3CCN(c4ccccc4)CC3)sc2c1] | 413.6 | 2-(6-Ethoxy-benzothiazol-2-ylsulfanyl)-1-(4-phenyl-piperazin-1-yl)-ethanone | C |
| 15 | 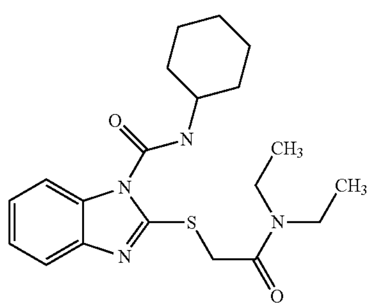 [SMILES: CCN(CC)C(=O)CSc1nc2ccccc2n1C(=O)NC1CCCCC1] | 388.5 | 2-Diethylcarbamoyl-methyl-sulfanyl-benzoimidazole-1-carboxylic acid cyclohexylamide | D |
| 16 | 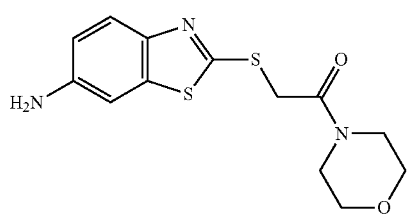 [SMILES: Nc1ccc2nc(SCC(=O)N3CCOCC3)sc2c1] | 309.4 | 2-(6-Amino-benzothiazol-2-ylsulfanyl)-1-morpholin-4-yl-ethanone | D |
| 17 | 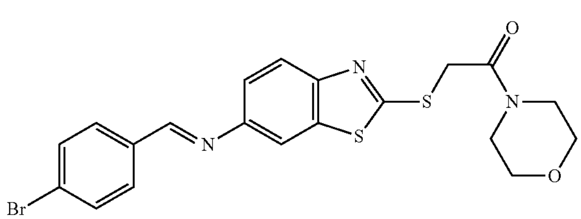 [SMILES: O=C(CSc1nc2ccc(/N=C/c3ccc(Cl)cc3)cc2s1)N1CCOCC1] | 476.4 | 2-(6-{[1-(4-Bromo-phenyl)-meth-(E)-ylidene]-amino}-benzothiazol-2-ylsulfanyl)-1-morpholin-4-yl-ethanone | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 18 | 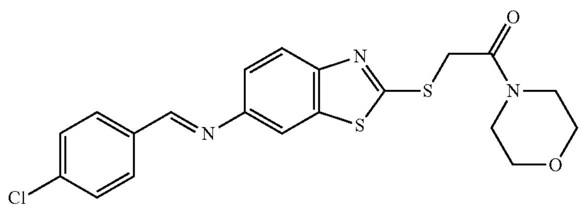 | 432.0 | 2-(6-{1-(4-Chloro-phenyl)-meth-(E)-ylidene]-amino}-benzothiazol-2-ylsulfanyl)-1-morpholin-4-yl-ethanone | D |
| 19 | 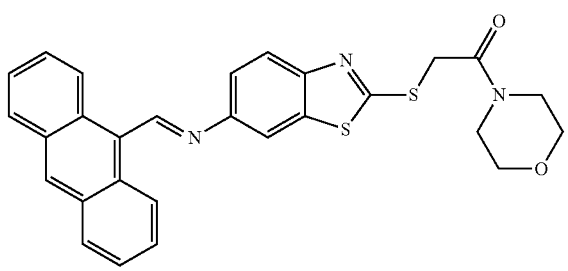 [SMILES: O=C(CSc1nc2ccc(/N=C/c3c4ccccc4cc4ccccc34)cc2s1)N1CCOCC1] | 497.6 | 2-(6-{[1-Anthracen-9-yl-meth-(E)-ylidene]-amino}-benzothiazol-2-ylsulfanyl)-1-morpholin-4-yl-ethanone | D |
| 20 | 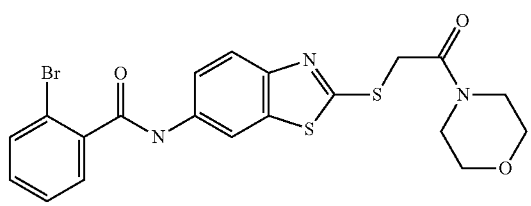 [SMILES: O=C(Nc1ccc2nc(SCC(=O)N3CCOCC3)sc2c1)c1ccccc1Br] | 492.4 | 2-Bromo-N-[2-(2-morpholin-4-yl-2-oxo-ethylsulfanyl)-benzothiazol-6-yl]-benzamide | D |
| 21 | 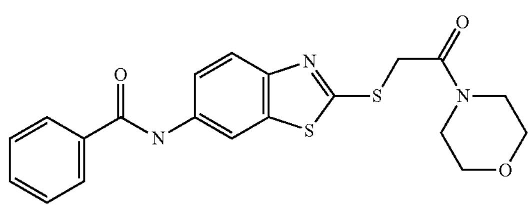 [SMILES: O=C(Nc1ccc2nc(SCC(=O)N3CCOCC3)sc2c1)c1ccccc1] | 413.5 | N-[2-(2-Morpholin-4-yl-2-oxo-ethylsulfanyl)-benzothiazol-6-yl)-benzamide | D |
| 22 | 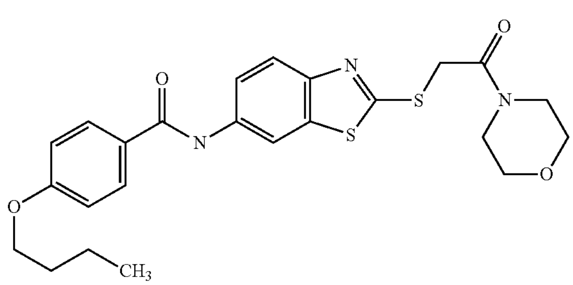 [SMILES: CCCCOc1ccc(C(=O)Nc2ccc3nc(SCC(=O)N4CCOCC4)sc3c2)cc1] | 485.6 | 4-Butoxy-N-[2-(2-morpholin-4-yl-2-oxo-ethylsulfanyl)-benzothiazol-6-yl]-benzamide | D |

TABLE 1-continued

List of compounds of the present invention and their anti-dengue 2 viral activity

| Compound | Chemical Structure | Molecular Weight | Chemical Name | Activity A: EC$_{50}$ ≤ 1 uM; B: 1 < EC$_{50}$ ≤ 10 uM; C: 10 < EC$_{50}$ ≤ 25 uM; D: EC$_{50}$ > 25 uM; n/a: Not determined |
|---|---|---|---|---|
| 23 | 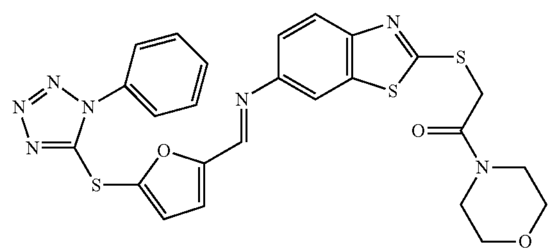 [SMILES: O=C(CSc1nc2ccc(/N=C/c3ccc(Sc4nnnn4-c4ccccc4)o3)cc2s1)N1CCOCC1] | 563.7 | 1-Morpholin-4-yl-2-(6-{[1-[5-(1-phenyl-1H-tetrazol-5-ylsulfanyl)-furan-2-yl]-meth-(E)-ylidene]-amino}-benzothiazol-2-ylsulfanyl)-ethanone | D |
| 24 | 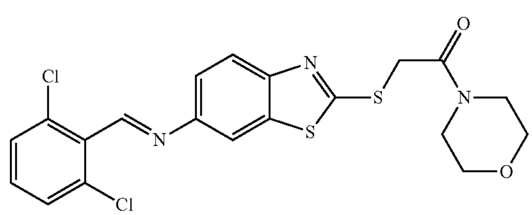 [SMILES: O=C(CSc1nc2ccc(/N=C/c3c(Cl)cccc3Cl)cc2s1)N1CCOCC1] | 466.4 | 2-(6-{[1-(2,6-Dichloro-phenyl)-meth-(E)-ylidene]-amino}-benzothiazol-2-ylsulfanyl)-1-morpholin-4-yl-ethanone | D |
| 25 | 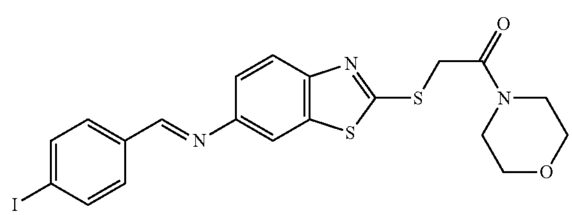 [SMILES: O=C(CSc1nc2ccc(/N=C/c3ccc(I)cc3)cc2s1)N1CCOCC1] | 523.4 | 2-(6-{[1-(4-Iodo-phenyl)-meth-(E)-ylidene]-amino}-benzothiazol-2-ylsulfanyl)-1-morpholin-4-yl-ethanone | D |
| 26 | 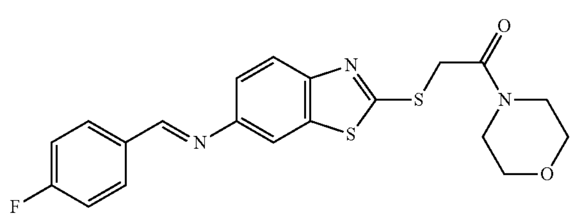 [SMILES: O=C(CSc1nc2ccc(/N=C/c3ccc(F)cc3)cc2s1)N1CCOCC1] | 415.5 | 2-(6-{[1-(4-Fluoro-phenyl)-meth-(E)-ylidene]-amino}-benzothiazol-2-ylsulfanyl)-1-morpholin-4-yl-ethanone | D |
| 27 | 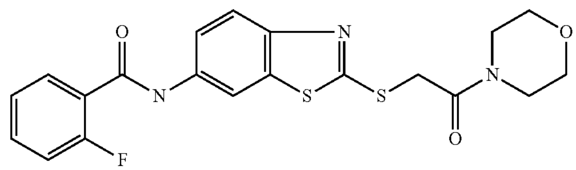 [SMILES: O=C(Nc1ccc2nc(SCC(=O)N3CCOCC3)sc2c1)c1ccccc1F] | 431.5 | 2-Fluoro-N-[2-(2-morpholin-4-yl-2-oxo-ethylsulfanyl)-benzothiazol-6-yl]-benzamide | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 28 | 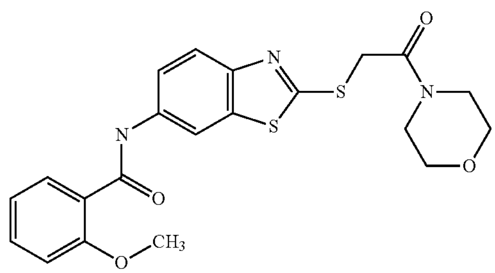 [SMILES: COc1ccccc1C(=O)Nc1ccc2nc(SCC(=O)N3CCOCC3)sc2c1] | 443.5 | 2-Methoxy-N-[2-(2-morpholin-4-yl-2-oxo-ethylsulfanyl)-benzothiazol-6-yl)-benzamide | D |
| 29 | 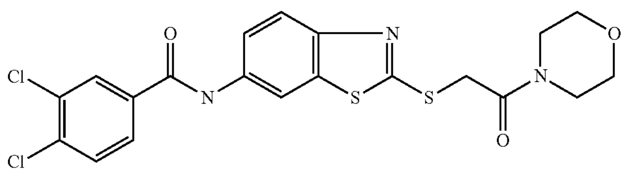 [SMILES: O=C(Nc1ccc2nc(SCC(=O)N3CCOCC3)sc2c1)c1ccc(Cl)c(Cl)c1] | 482.4 | 3,4-Dichloro-N-[2-(2-morpholin-4-yl-2-oxo-ethylsulfanyl)-benzothiazol-6-yl]-benzamide | D |
| 30 | 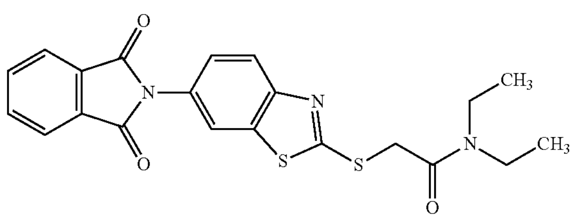 [SMILES: CCN(CC)C(=O)CSc1nc2ccc(N3C(=O)c4ccccc4C3=O)cc2s1] | 425.5 | 2-[6-(1,3-Dioxo-1,3-dihydro-isoindol-2-yl)-benzothiazol-2-ylsulfanyl]-N,N-diethyl-acetamide | D |
| 31 | 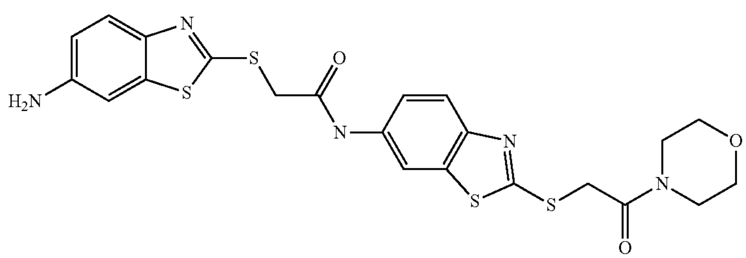 [SMILES: Nc1ccc2nc(SCC(=O)Nc3ccc4nc(SCC(=O)N5CCOCC5)sc4c3)sc2c1] | 531.7 | 2-(6-Amino-benzothiazol-2-ylsulfanyl)-N-[2-(2-morpholin-4-yl-2-oxo-ethylsulfanyl)-benzothiazol-6-yl]-acetamide | D |
| 32 | 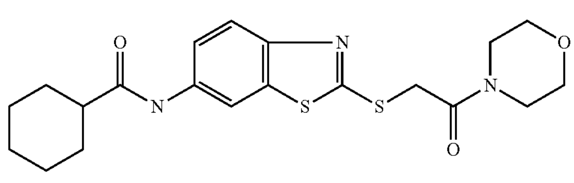 [SMILES: O=C(Nc1ccc2nc(SCC(=O)N3CCOCC3)sc2c1)C1CCCCC1] | 419.6 | Cyclohexane-carboxylic acid [2-(2-morpholin-4-yl-2-oxo-ethylsulfanyl)-benzothiazol-6-yl]-amide | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 33 | 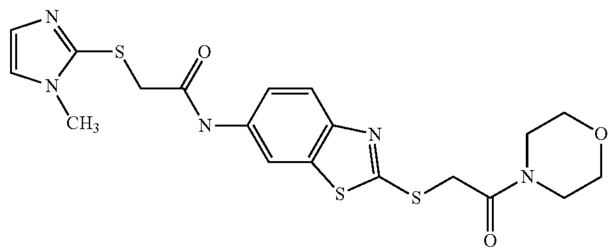 [SMILES: Cn1ccnc1SCC(=O)Nc1ccc2nc(SCC(=O)N3CCOCC3)sc2c1] | 463.6 | 2-(1-Methyl-1H-imidazol-2-ylsulfanyl)-N-[2-(2-morpholin-4-yl-2-oxo-ethylsulfanyl)-benzothiazol-6-yl]-acetamide | D |
| 34 | 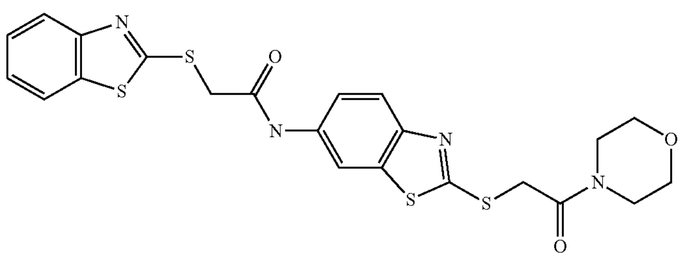 [SMILES: O=C(CSc1nc2ccccc2s1)Nc1ccc2nc(SCC(=O)N3CCOCC3)sc2c1] | 516.7 | 2-(Benzothiazol-2-sulfanyl)-N-[2-(2-morpholin-4-yl-2-oxo-ethylsulfanyl)-benzothiazol-6-yl]-acetamide | D |
| 35 | 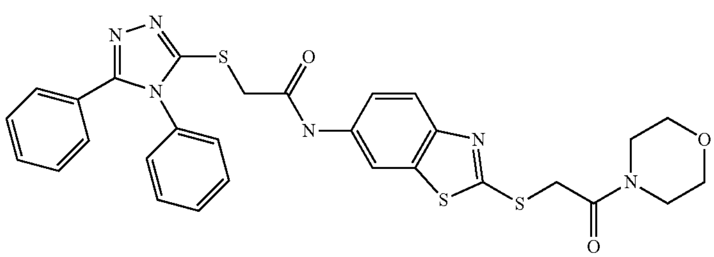 [SMILES: O=C(CSc1nnc(-c2ccccc2)n1-c1ccccc1)Nc1ccc2nc(SCC(=O)N3CCOCC3)sc2c1] | 602.8 | 2-(4,5-Diphenyl-4H-[1,2,4]triazol-3-ylsulfanyl)-N-[2-(2-morpholin-4-yl-2-oxo-ethylsulfanyl)-benzothiazol-6-yl]-acetamide | D |
| 36 | 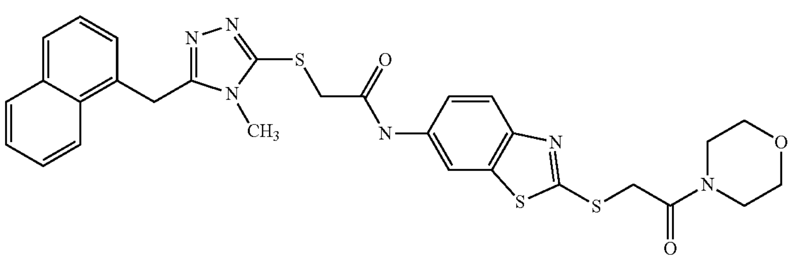 [SMILES: Cn1c(Cc2cccc3ccccc23)nnc1SCC(=O)Nc1ccc2nc(SCC(=O)N3CCOCC3)sc2c1] | 604.8 | 2-(4-Methyl-5-naphthalen-1-ylmethyl-4H-[1,2,4]triazol-3-ylsulfanyl)-N-[2-(2-morpholin-4-yl-2-oxo-ethylsulfanyl)-benzothiazol-6-yl]-acetamide | D |
| 37 | 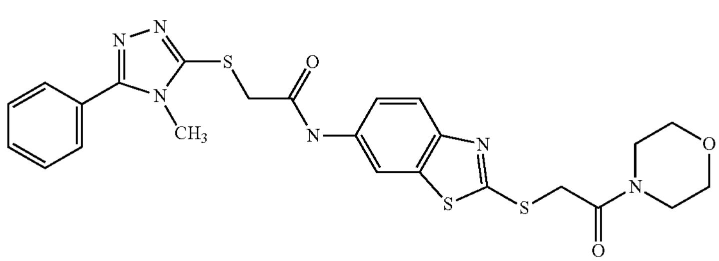 [SMILES: Cn1c(SCC(=O)Nc2ccc3nc(SCC(=O)N4CCOCC4)sc3c2)nnc1-c1ccccc1] | 540.7 | 2-(4-Methyl-5-phenyl-4H-[1,2,4]triazol-3-ylsulfanyl)-N-[2-(2-morpholin-4-yl-2-oxo-ethylsulfanyl)-benzothiazol-6-yl]-acetamide | D |

TABLE 1-continued

List of compounds of the present invention and their anti-dengue 2 viral activity

| Compound | Chemical Structure | Molecular Weight | Chemical Name | Activity A: EC$_{50}$ ≤ 1 uM; B: 1 < EC$_{50}$ ≤ 10 uM; C: 10 < EC$_{50}$ ≤ 25 uM; D: EC$_{50}$ > 25 uM; n/a: Not determined |
|---|---|---|---|---|
| 38 | 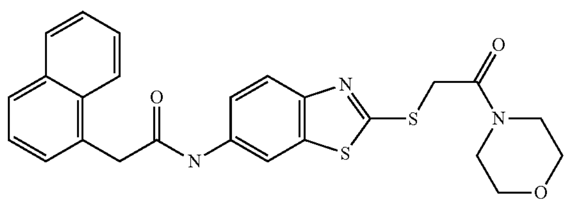 [SMILES: O=C(Cc1cccc2ccccc12)Nc1ccc2nc(SCC(=O)N3CCOCC3)sc2c1] | 477.6 | N-[2-(2-Morpholin-4-yl-2-oxo-ethylsulfanyl)-benzothiazol-6-yl]-2-naphthalen-1-yl-acetamide | D |
| 39 | 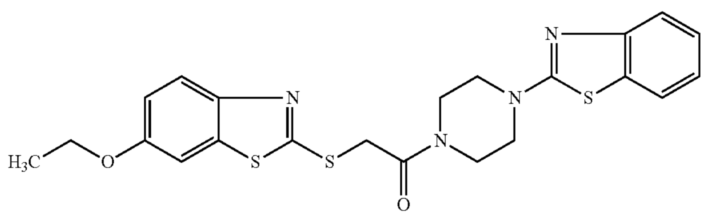 [SMILES: CCOc1ccc2nc(SCC(=O)N3CCN(c4nc5ccccc5s4)CC3)sc2c1] | 470.6 | 1-(4-Benzothiazol-2-yl-piperazin-1-yl)-2-(6-ethoxy-benzothiazol-2-ylsulfanyl)-ethanone | D |
| 40 | 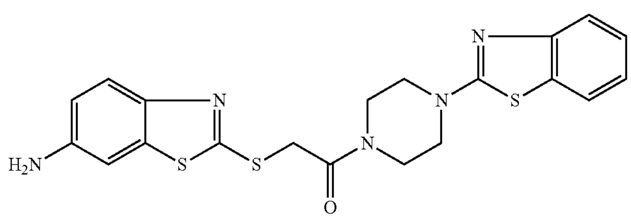 [SMILES: Nc1ccc2nc(SCC(=O)N3CCN(c4nc5ccccc5s4)CC3)sc2c1] | 441.6 | 2-(6-Amino-benzothiazol-2-ylsulfanyl)-1-(4-benzothiazol-2-yl-piperazin-1-yl)-ethanone | D |
| 41 | 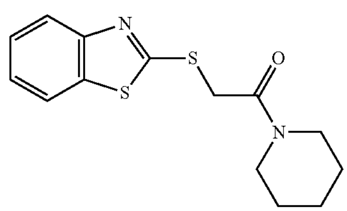 [SMILES: O=C(CSc1nc2ccccc2s1)N1CCCCC1] | 292.4 | 2-(Benzothiazol-2-ylsulfanyl)-1-piperidin-1-yl-ethanone | D |
| 42 | 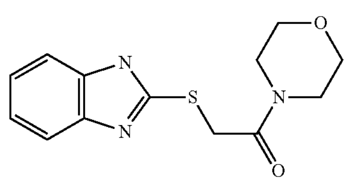 [SMILES: O=C(CSc1nc2ccccc2[nH]1)N1CCOCC1] | 277.3 | 2-(1H-Benzo-imidazol-2-ylsulfanyl)-1-morpholin-4-yl-ethanone | D |
| 43 | 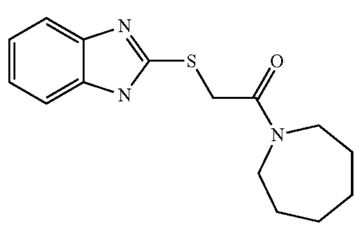 [SMILES: O=C(CSc1nc2ccccc2[nH]1)N1CCCCCC1] | 289.4 | 1-Azepan-1-yl-2-(1H-benzo-imidazol-2-ylsulfanyl)-ethanone | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 44 | 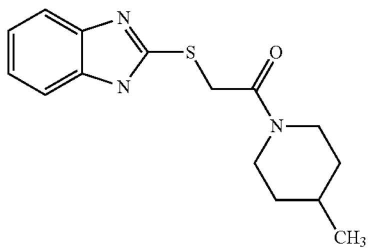 [SMILES: CC1CCN(C(=O)CSc2nc3ccccc3[nH]2)CC1] | 289.4 | 2-(1H-Benzoimidazol-2-ylsulfanyl)-1-(4-methyl-piperidin-1-yl)-ethanone | D |
| 45 | 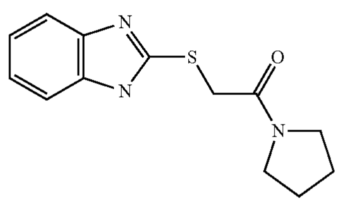 [SMILES: O=C(CSc1nc2ccccc2[nH]1)N1CCCC1] | 261.3 | 2-(1H-Benzoimidazol-2-ylsulfanyl)-1-pyrrolidin-1-yl-ethanone | D |
| 46 | 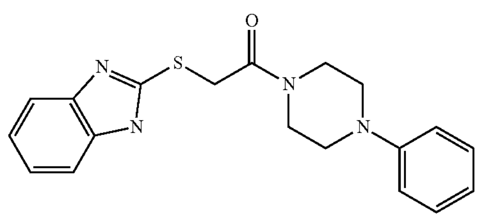 [SMILES: O=C(CSc1nc2ccccc2[nH]1)N1CCN(c2ccccc2)CC1] | 352.5 | 2-(1H-Benzoimidazol-2-ylsulfanyl)-1-(4-phenyl-piperazin-1-yl)-ethanone | D |
| 47 | 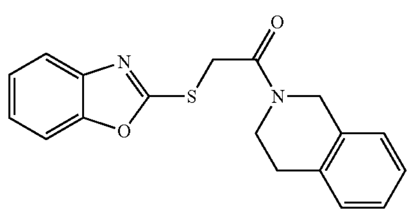 [SMILES: O=C(CSc1nc2ccccc2o1)N1CCc2ccccc2C1] | 324.4 | 2-(Benzooxazol-2-ylsulfanyl)-1-(3,4-dihydro-1H-isoquinolin-2-yl)-ethanone | D |
| 48 | 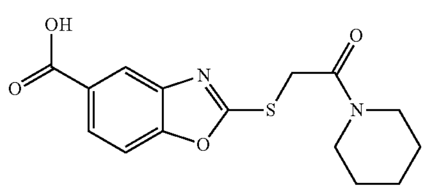 [SMILES: O=C(O)c1ccc2oc(SCC(=O)N3CCCCC3)nc2c1] | 320.4 | 2-(2-Oxo-2-piperidin-1-yl-ethylsulfanyl)-benzooxazole-5-carboxylic acid | D |
| 49 | 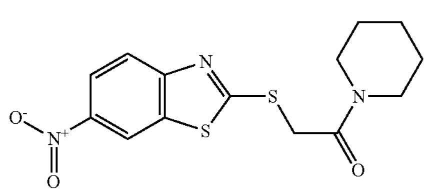 [SMILES: O=C(CSc1nc2ccc([N+](=O)[O-])cc2s1)N1CCCCC1] | 337.4 | 2-(6-Nitro-benzothiazol-2-ylsulfanyl)-1-piperidin-1-yl-ethanone | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 50 | 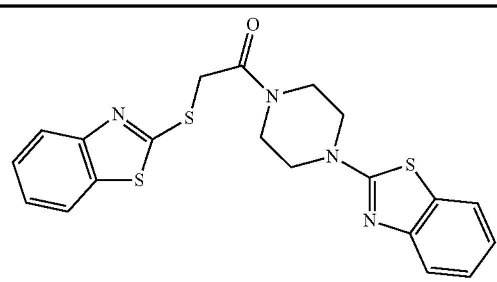 | 426.6 | 1-(4-Benzothiazol-2-yl-piperazin-1-yl)-2-(benzothiazol-2-ylsulfanyl)-ethanone | D |
| 51 | 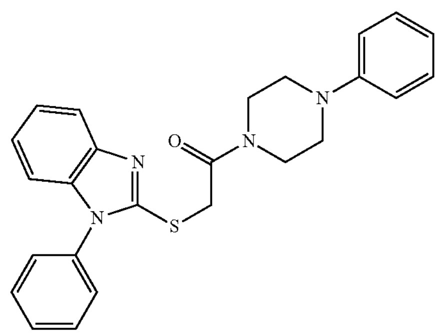 [SMILES: O=C(CSc1nc2ccccc2n1-c1ccccc1)N1CCN(c2ccccc2)CC1] | 428.6 | 2-(1-Phenyl-1H-benzoimidazol-2-ylsulfanyl)-1-(4-phenyl-piperazin-1-yl)-ethanone | D |
| 52 | 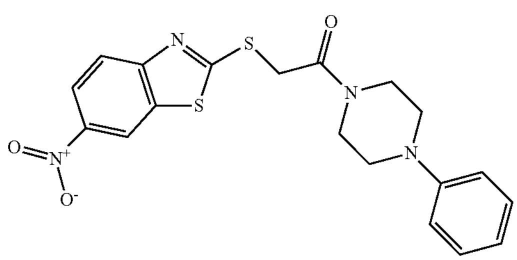 [SMILES: O=C(CSc1nc2ccc([N+](=O)[O-])cc2s1)N1CCN(c2ccccc2)CC1] | 414.5 | 2-(6-Nitro-benzothiazol-2-ylsulfanyl)-1-(4-phenyl-piperazin-1-yl)-ethanone | D |
| 53 | 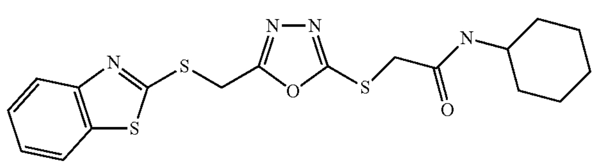 [SMILES: O=C(CSc1nnc(CSc2nc3ccccc3s2)o1)NC1CCCCC1] | 420.6 | 2-[5-(Benzothiazol-2-ylsulfanyl-methyl)-[1,3,4]oxadiazol-2-ylsulfanyl]-N-cyclohexyl-acetamide | D |
| 54 | 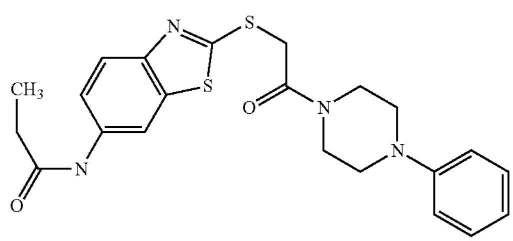 [SMILES: CCC(=O)Nc1ccc2nc(SCC(=O)N3CCN(c4ccccc4)CC3)sc2c1] | 440.6 | N-{2-[2-Oxo-2-(4-phenyl-piperazin-1-yl)-ethylsulfanyl]-benzothiazol-6-yl}-propionamide | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 55 | 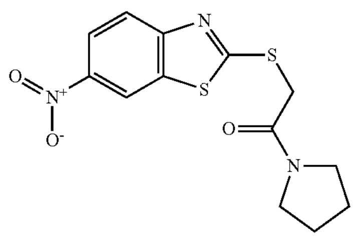 [SMILES: O=C(CSc1nc2ccc([N+](=O)[O-])cc2s1)N1CCCC1] | 323.4 | 2-(6-Nitro-benzothiazol-2-ylsulfanyl)-1-pyrrolidin-1-yl-ethanone | D |
| 56 | 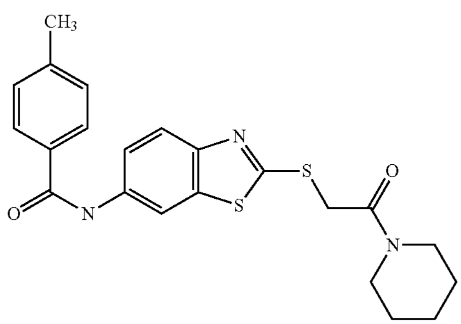 [SMILES: Cc1ccc(C(=O)Nc2ccc3nc(SCC(=O)N4CCCCC4)sc3c2)cc1] | 425.6 | 4-Methyl-N-[2-(2-oxo-2-piperidin-1-yl-ethylsulfanyl)-benzothiazol-6-yl]-benzamide | D |
| 57 | 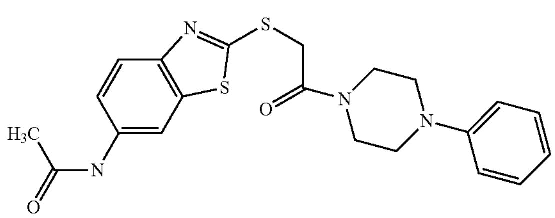 [SMILES: CC(=O)Nc1ccc2nc(SCC(=O)N3CCN(c4ccccc4)CC3)sc2c1] | 426.6 | N-{2-[2-Oxo-2-(4-phenyl-piperazin-1-yl)-ethylsulfanyl]-benzothiazol-6-yl}-acetamide | D |
| 58 | 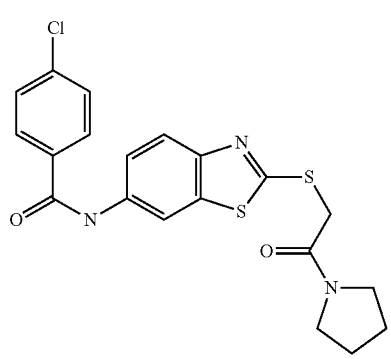 [SMILES: O=C(Nc1ccc2nc(SCC(=O)N3CCCC3)sc2c1)c1ccc(Cl)cc1] | 432.0 | 4-Chloro-N-[2-(2-oxo-2-pyrrolidin-1-yl-ethylsulfanyl)-benzothiazol-6-yl]-benzamide | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 59 | 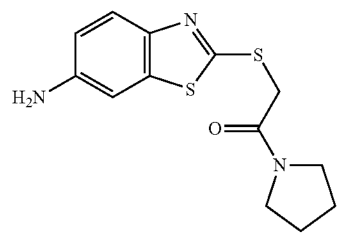 [SMILES: Nc1ccc2nc(SCC(=O)N3CCCC3)sc2c1] | 293.4 | 2-(6-Amino-benzothiazol-2-ylsulfanyl)-1-pyrrolidin-1-yl-ethanone | D |
| 60 | 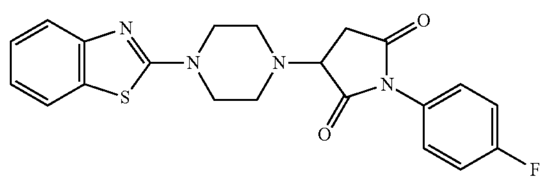 [SMILES: O=C1CC(N2CCN(c3nc4ccccc4s3)CC2)C(=O)N1c1ccc(F)cc1] | 410.5 | 3-(4-Benzothiazol-2-yl-piperazin-1-yl)-1-(4-fluoro-phenyl)-pyrrolidine-2,5-dione | D |
| 61 | 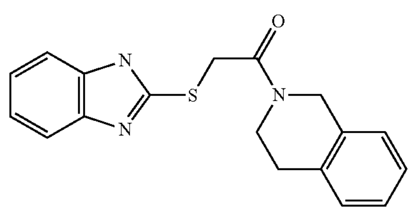 [SMILES: O=C(CSc1nc2ccccc2[nH]1)N1CCc2ccccc2C1] | 323.4 | 2-(1H-Benzoimidazol-2-ylsulfanyl)-1-(3,4-dihydro-1H-isoquinolin-2-yl)-ethanone | D |
| 62 | 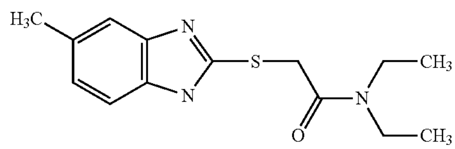 [SMILES: CCN(CC)C(=O)CSc1nc2cc(C)ccc2[nH]1] | 277.4 | N,N-Diethyl-2-(5-methyl-1H-benzoimidazol-2-ylsulfanyl)-acetamide | D |
| 63 | 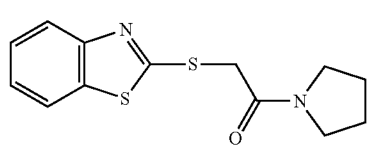 [SMILES: O=C(CSc1nc2ccccc2s1)N1CCCC1] | 278.4 | 2-(Benzothiazol-2-ylsulfanyl)-1-pyrrolidin-1-yl-ethanone | D |
| 64 | 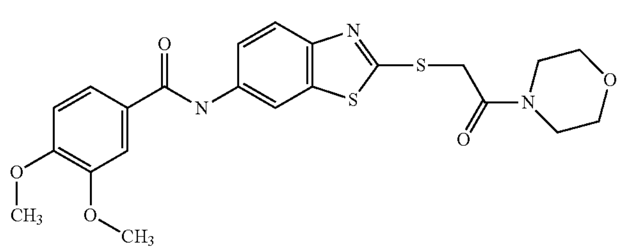 [SMILES: COc1ccc(C(=O)Nc2ccc3nc(SCC(=O)N4CCOCC4)sc3c2)cc1OC] | 473.6 | 3,4-Dimethoxy-N-[2-(2-morpholin-4-yl-2-oxo-ethylsulfanyl)-benzothiazol-6-yl]-benzamide | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 65 | 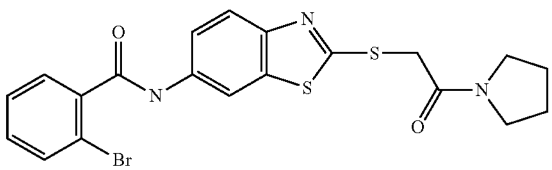 [SMILES: O=C(Nc1ccc2nc(SCC(=O)N3CCCC3)sc2c1)c1ccccc1Br] | 476.4 | 2-Bromo-N-[2-(2-oxo-2-pyrrolidin-1-yl-ethylsulfanyl)-benzothiazol-6-yl]-benzamide | D |
| 66 | 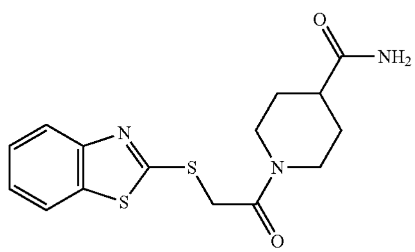 | 335.5 | 1-[2-(Benzothiazol-2-ylsulfanyl)-acetyl]-piperidine-4-carboxylic acid amide | D |
| 67 | 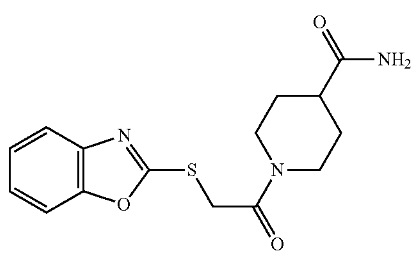 | 319.4 | 1-[2-(Benzooxazol-2-ylsulfanyl)-acetyl]-piperidine-4-carboxylic acid amide | D |
| 68 | 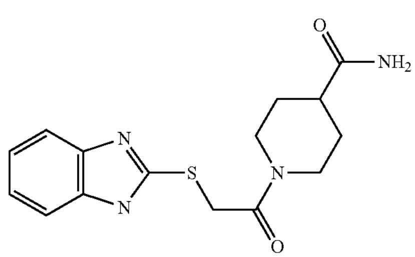 [SMILES: NC(=O)C1CCN(C(=O)CSc2nc3ccccc3s2)CC1] | 318.4 | 1-[2-(1H-Benzoimidazol-2-ylsulfanyl)-acetyl]-piperidine-4-carboxylic acid amide | D |
| 69 | 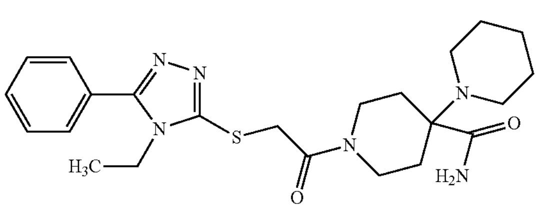 [SMILES: CCn1c(SCC(=O)N2CCC(C(N)=O)(N3CCCCC3)CC2)nnc1-c1ccccc1] | 456.6 | 1'-[2-(4-Ethyl-5-phenyl-4H-[1,2,4]triazol-3-ylsulfanyl)-acetyl]-[1,4']bipiperidinyl-4'-carboxylic acid amide | D |

TABLE 1-continued

List of compounds of the present invention and their anti-dengue 2 viral activity

| Compound | Chemical Structure | Molecular Weight | Chemical Name | Activity A: EC$_{50}$ ≤ 1 uM; B: 1 < EC$_{50}$ ≤ 10 uM; C: 10 < EC$_{50}$ ≤ 25 uM; D: EC$_{50}$ > 25 uM; n/a: Not determined |
|---|---|---|---|---|
| 70 | 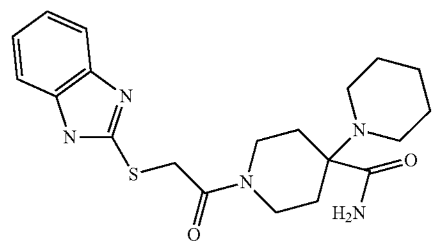 [SMILES: NC(=O)C1(N2CCCCC2)CCN(C(=O)CSc2nc3ccccc3[nH]2)CC1] | 401.5 | 1'-[2-(1H-Benzo-imidazol-2-ylsulfanyl)-acetyl]-[1,4']bipiperidinyl-4'-carboxylic acid amide | D |
| 71 | 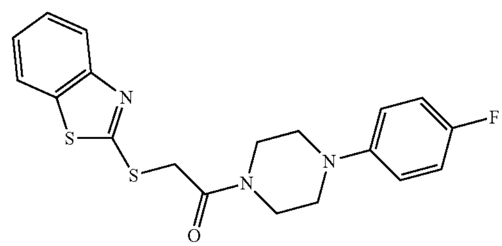 | 387.5 | 2-(Benzothiazol-2-ylsulfanyl)-1-[4-(4-fluoro-phenyl)-piperazin-1-yl]-ethanone | D |
| 72 | 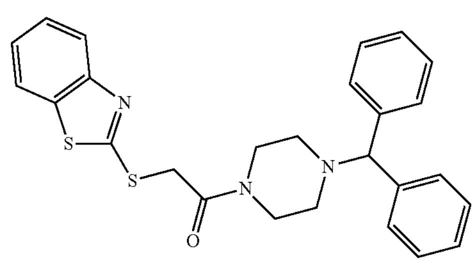 [SMILES: O=C(CSc1nc2ccccc2s1)N1CCN(C(c2ccccc2)c2ccccc2)CC1] | 459.6 | 1-(4-Benzhydryl-piperazin-1-yl)-2-(benzothiazol-2-ylsulfanyl)-ethanone | D |
| 73 | 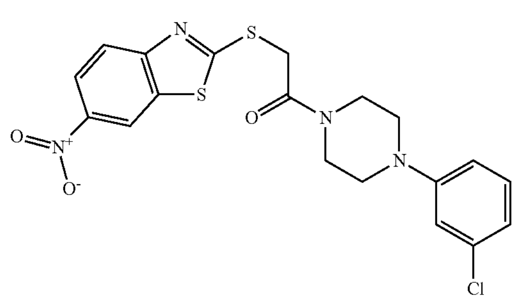 [SMILES: O=C(CSc1nc2ccc([N+](=O)[O-])cc2s1)N1CCN(c2cccc(Cl)c2)CC1] | 449.0 | 1-[4-(3-Chloro-phenyl)-piperazin-1-yl]-2-(6-nitro-benzothiazol-2-ylsulfanyl)-ethanone | D |
| 74 | 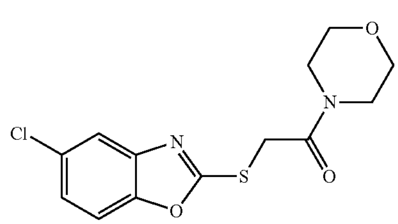 [SMILES: O=C(CSc1nc2cc(Cl)ccc2o1)N1CCOCC1] | 312.8 | 2-(5-Chloro-benzooxazol-2-ylsulfanyl)-1-morpholin-4-yl-ethanone | D |

TABLE 1-continued

List of compounds of the present invention and their anti-dengue 2 viral activity

| Compound | Chemical Structure | Molecular Weight | Chemical Name | Activity A: $EC_{50} \leq$ 1 uM; B: $1 < EC_{50} \leq$ 10 uM; C: $10 < EC_{50} \leq$ 25 uM; D: $EC_{50} >$ 25 uM; n/a: Not determined |
|---|---|---|---|---|
| 75 | 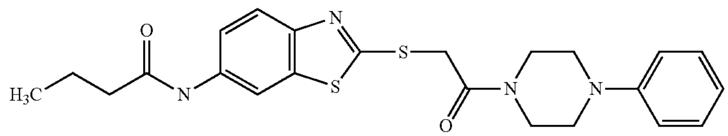 [SMILES: CCCC(=O)Nc1ccc2nc(SCC(=O)N3CCN(c4ccccc4)CC3)sc2c1] | 454.6 | N-{2-[2-Oxo-2-(4-phenyl-piperazin-1-yl)-ethylsulfanyl]-benzothiazol-6-yl}-butyramide | D |
| 76 | 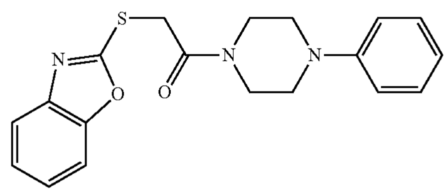 [SMILES: O=C(CSc1nc2ccccc2o1)N1CCN(c2ccccc2)CC1] | 353.4 | 2-(Benzooxazol-2-ylsulfanyl)-1-(4-phenyl-piperazin-1-yl)-ethanone | D |
| 77 | 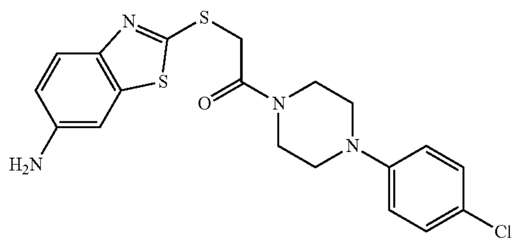 [SMILES: Nc1ccc2nc(SCC(=O)N3CCN(c4ccc(Cl)cc4)CC3)sc2c1] | 419.0 | 2-(6-Amino-benzothiazol-2-ylsulfanyl)-1-[4-(4-chloro-phenyl)-piperazin-1-yl]-ethanone | D |
| 78 | 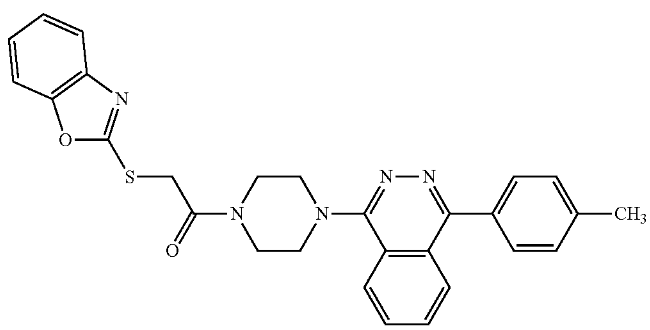 [SMILES: Cc1ccc(-c2nnc(N3CCN(C(=O)CSc4nc5ccccc5o4)CC3)c3ccccc23)cc1] | 495.6 | 2-(Benzooxazol-2-ylsulfanyl)-1-[4-(4-p-tolyl-phthalazin-1-yl)-piperazin-1-yl]-ethanone | D |
| 79 | 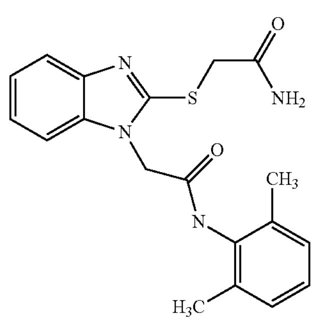 [SMILES: Cc1cccc(C)c1NC(=O)Cn1c(SCC(N)=O)nc2ccccc21] | 368.5 | 2-(1-[(2,6-Dimethyl-phenyl-carbamoyl)-methyl]-1H-benzo-imidazol-2-ylsulfanyl]-acetamide | D |

TABLE 1-continued

List of compounds of the present invention and their anti-dengue 2 viral activity

| Compound | Chemical Structure | Molecular Weight | Chemical Name | Activity A: EC$_{50}$ ≤ 1 uM; B: 1 < EC$_{50}$ ≤ 10 uM; C: 10 < EC$_{50}$ ≤ 25 uM; D: EC$_{50}$ > 25 uM; n/a: Not determined |
|---|---|---|---|---|
| 80 | 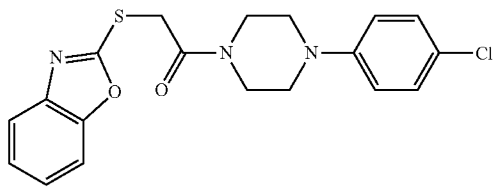 [SMILES: O=C(CSc1nc2ccccc2o1)N1CCN(c2ccc(Cl)cc2)CC1] | 387.9 | 2-(Benzooxazol-2-ylsulfanyl)-1-[4-(4-chloro-phenyl)-piperazin-1-yl]-ethanone | D |
| 81 | 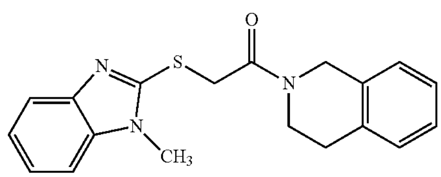 [SMILES: Cn1c(SCC(=O)N2CCc3ccccc3C2)nc2ccccc21] | 337.4 | 1-(3,4-Dihydro-1H-isoquinolin-2-yl)-2-(1-methyl-1H-benzoimidazol-2-ylsulfanyl)-ethanone | D |
| 82 | 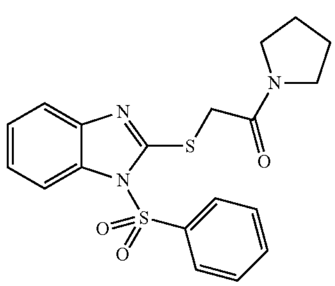 [SMILES: O=C(CSc1nc2ccccc2n1S(=O)(=O)c1ccccc1)N1CCCC1] | 401.5 | 2-(1-Benzenesulfonyl-1H-benzoimidazol-2-ylsulfanyl)-1-pyrrolidin-1-yl-ethanone | n/a |

REFERENCES

1. Barth, O. M. 1999. Ultrastructural aspects of the dengue virus (flavivirus) particle morphogenesis. J Submicrosc Cytol Pathol 31:407-12.
2. Benarroch, D., M. P. Egloff, L. Mulard, C. Guerreiro, J. L. Romette, and B. Canard. 2004. A structural basis for the inhibition of the NS5 dengue virus mRNA 2'-O-methyl-transferase domain by ribavirin 5'-triphosphate. J Biol Chem 279:35638-43.
3. Brinton, M. A., and J. H. Dispoto. 1988. Sequence and secondary structure analysis of the 5'-terminal region of flavivirus genome RNA. Virology 162:290-9.
4. CDC. 2005. Dengue Fever, http://www2.ncid.cdc.gov/travel/yb/utils/ybGet.asp?section=dis&obj=dengue.htm.
5. Edelman, R., S. S. Wasserman, S. A. Bodison, R. J. Putnak, K. H. Eckels, D. Tang, N. Kanesa-Thasan, D. W. Vaughn, B. L. Innis, and W. Sun. 2003. Phase I trial of 16 formulations of a tetravalent live-attenuated dengue vaccine. Am J Trop Med Hyg 69:48-60.
6. Falgout, B., M. Pethel, Y. M. Zhang, and C. J. Lai. 1991. Both nonstructural proteins NS2B and NS3 are required for the proteolytic processing of dengue virus nonstructural proteins. J Virol 65:2467-75.
7. Fink, J., F. Gu, and S. G. Vasudevan. 2006. Role of T cells, cytokines and antibody in dengue fever and dengue haemorrhagic fever. Rev Med Virol 16:263-75.
8. Halstead, S. B. 1988. Pathogenesis of dengue: challenges to molecular biology. Science 239:476-81.
9. Hase, T., P. L. Summers, K. H. Eckels, and W. B. Baze. 1987. An electron and immunoelectron microscopic study of dengue-2 virus infection of cultured mosquito cells: maturation events. Arch Virol 92:273-91.
10. Hillen, W., G. Klock, I. Kaffenberger, L. V. Wray, and W. S. Reznikoff. 1982. Purification of the TET repressor and TET operator from the transposon Tn10 and characterization of their interaction. J Biol Chem 257:6605-13.
12. Kanesa-thasan, N., W. Sun, G. Kim-Ahn, S. Van Albert, J. R. Putnak, A. King, B. Raengsakulsrach, H. Christ-Schmidt, K. Gilson, J. M. Zahradnik, D. W. Vaughn, B. L. Innis, J. F. Saluzzo, and C. H. Hoke, Jr. 2001. Safety and immunogenicity of attenuated dengue virus vaccines (Aventis Pasteur) in human volunteers. Vaccine 19:3179-88.
13. Kitchener, S., M. Nissen, P. Nasveld, R. Forrat, S. Yoksan, J. Lang, and J. F. Saluzzo. 2006. Immunogenicity and safety of two live-attenuated tetravalent dengue vaccine formulations in healthy Australian adults. Vaccine 24:1238-41.
14. Koff, W. C., J. L. Elm, Jr., and S. B. Halstead. 1982. Antiviral effects if ribavirin and 6-mercapto-9-tetrahydro-2-furylpurine against dengue viruses in vitro. Antiviral Res 2:69-79.
15. Koff, W. C., R. D. Pratt, J. L. Elm, Jr., C. N. Venkateshan, and S. B. Halstead. 1983. Treatment of intracranial dengue virus infections in mice with a lipophilic derivative of ribavirin. Antimicrob Agents Chemother 24:134-6.
16. Leitmeyer, K. C., D. W. Vaughn, D. M. Watts, R. Salas, I. Villalobos, C. de, C. Ramos, and R. Rico-Hesse. 1999. Dengue virus structural differences that correlate with pathogenesis. J Virol 73:4738-47.
17. Malinoski, F. J., S. E. Hasty, M. A. Ussery, and J. M. Dalrymple. 1990. Prophylactic ribavirin treatment of dengue type 1 infection in rhesus monkeys. Antiviral Res 13:139-49.
18. Markoff, L., A. Chang, and B. Falgout. 1994. Processing of flavivirus structural glycoproteins: stable membrane insertion of premembrane requires the envelope signal peptide. Virology 204:526-40.
19. Medin, C. L., K. A. Fitzgerald, and A. L. Rothman. 2005. Dengue virus nonstructural protein NS5 induces interleukin-8 transcription and secretion. J Virol 79:11053-61.
20. Modis, Y., S. Ogata, D. Clements, and S. C. Harrison. 2003. A ligand-binding pocket in the dengue virus envelope glycoprotein. Proc Natl Acad Sci USA 100:6986-91.
21. Monath, T. P. 1994. Dengue: the risk to developed and developing countries. Proc Natl Acad Sci USA 91:2395-400.
22. Mukhopadhyay, S., R. J. Kuhn, and M. G. Rossmann. 2005. A structural perspective of the flavivirus life cycle. Nat Rev Microbial 3:13-22.
24. PAHO. 2006. Dengue and dengue hemorrhagic fever http://www.paho.org/english/ad/dpc/cd/dengue.htm.
25. Raviprakash, K., M. Sinha, C. G. Hayes, and K. R. Porter. 1998. Conversion of dengue virus replicative form RNA (RF) to replicative intermediate (RI) by nonstructural proteins NS-5 and NS-3. Am J Trop Med Hyg 58:90-5.
26. Rothman, A. L., and F. A. Ennis. 1999. Immunopathogenesis of Dengue hemorrhagic fever. Virology 257:1-6.
28. Sabchareon, A., J. Lang, P. Chanthavanich, S. Yoksan, R. Forrat, P. Attanath, C. Sirivichayakul, K. Pengsaa, C. Pojjaroen-Anant, W. Chokejindachai, A. Jagsudee, J. F. Saluzzo, and N. Bhamarapravati. 2002. Safety and immunogenicity of tetravalent live-attenuated dengue vaccines in That adult volunteers: role of serotype concentration, ratio, and multiple doses. Am J Trop Med Hyg 66:264-72.
29. Schlesinger, S., and M. J. Schlesinger. 1990. Replication of togaviridae and flaviviridae, p. 697-710. In B. N. Fields, D. M. Knipe, R. M. Chanock, M. S. Hirsch, J. L. Melnick, T. P. Monath, and B. Roizrnan (ed.), Virology, 2 ed, vol. 1. Ravens Press, New York.
30. O'Brien, J., I. Wilson, T. Orton, and F. Pognan. 2000. Investigation of the Alamar Blue (reazurin) fluorescent dye for the assessment of mammalian cell cytotoxicity. Eur J. Biochem. 267:5421-5426.
32. Takhampunya, R., S. Ubol, H. S. Houng, C. E. Cameron, and R. Padmanabhan. 2006. Inhibition of dengue virus replication by mycophenolic acid and ribavirin. J Gen Viral 87:1947-52.
33. Thein, S., M. M. Aung, T. N. Shwe, M. Aye, A. Zaw, K. Aye, K. M. Aye, and J. Aaskov. 1997. Risk factors in dengue shock syndrome. Am J Trop Med Hyg 56:566-72.
34. Uchil, P. D., and V. Satchidanandam. 2003. Architecture of the flaviviral replication complex. Protease, nuclease, and detergents reveal encasement within double-layered membrane compartments. J Biol Chem 278:24388-98.
35. Umareddy, I., A. Chao, A. Sampath, F. Gu, and S. G. Vasudevan. 2006. Dengue virus NS4B interacts with NS3 and dissociates it from single-stranded RNA. J Gen Viral 87:2605-14.
36. Whitby, K., T. C. Pierson, B. Geiss, K. Lane, M. Engle, Y. Zhou, R. W. Doms, and M. S. Diamond. 2005. Castanospermine, a potent inhibitor of dengue virus infection in vitro and in vivo. J Viral 79:8698-706.
37. WHO. 2002. Dengue and dengue haemorrhagic fever, http:/www.who.int/mediacentre/factsheets/fs117/en/.
38. WHO. 1997. Dengue haemorrhagic fever, http://www.who.int/csr/resources/publications/dengue/Denguication/en/index html.

All references cited herein are herein incorporated by reference in their entirety for all purposes.

The invention has been described in terms of preferred embodiments thereof, but is more broadly applicable as will be understood by those skilled in the art. The scope of the invention is only limited by the following claims.

What is claimed is:

1. A method for the treatment of a Dengue virus infection, comprising administering in a therapeutically effective amount to a mammal in need thereof, a compound of Formula I below or a pharmaceutically acceptable salt thereof:

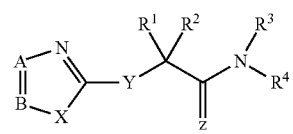

Formula I wherein A is C—R$^5$ and B is C—R$^6$, wherein R$^5$ and R$^6$ are independently selected from the group consisting of hydrogen, substituted or unsubstituted alkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylammo, heteroarylamino, acylamino, arylacylamino, heteroarylacylamino, alkylsulfonylammo, arylsulfonylamino, acyl, arylacyl, heteroarylacyl, alkylsulflnyl, arylsulflnyl, heteroarylsulflnyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano, and nitro, or optionally R$^5$ and R$^6$ together with the carbons they are attached to form a substituted or unsubstituted ring, which may be aromatic or non-aromatic and optionally includes one or more heteroatoms in the ring and is optionally is fused with an aromatic or aliphatic ring;

X and Z are independently selected from the group consisting of O, S and N—R$^7$, wherein R$^7$ is selected from the group consisting of hydrogen, alkyl, alkenyl, alkynyl, cycloalkyl, heterocycloalkyl, arylalkyl, aryl, heteroaryl, acyl, arylacyl, heteroarylacyl, sulfonyl, aminosulfonyl, substituted aminosulfonyl, alkoxycarbonyl, cycloalkyloxycarbonyl, aryloxycarbonyl, carbamoyl, and substituted carbamoyl, and Y is S;

R¹ and R² are independently selected from the group consisting of hydrogen, substituted or unsubstituted alkyl, alkenyl, alkynyl, cycloalkyl, heterocycloalkyl, arylalkyl, aryl, heteroaryl, alkyloxy, aryloxy, heteroaryloxy, acyloxy, arylacyloxy, heteroarylacyloxy, alkylsulfonyloxy, arylsulfonyloxy, alkylthio, arylthio, alkylammo, dialkylammo, cycloalkylamino, heterocycloalkylammo, arylammo, heteroarylammo, acylamino, arylacylamino, heteroarylacylamino, alkylsulfonylammo, arylsulfonylamino, acyl, arylacyl, heteroarylacyl, alkylsulflnyl, arylsulflnyl, heteroarylsulfmyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, cyano, isocyano, and nitro, or optionally R¹ and R² together with the carbon they are attached to may form a substituted or unsubstituted ring, which optionally includes one or more heteroatoms in the ring and optionally is fused with an aromatic or aliphatic ring;

R³ and R⁴ are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulflnyl, arylsulflnyl, heteroarylsulflnyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl, and substituted carbamoyl, or optionally R³ and R⁴ together with the nitrogen atom they are attached to form a substituted or unsubstituted ring, which optionally includes one or more heteroatoms in the ring and optionally is fused with an aromatic or aliphatic ring; and R¹ or R² and R³ or R⁴ together with the carbon or nitrogen they are attached to and the carbon that Z is attached to optionally form a substituted or unsubstituted ring, which optionally includes one or more heteroatoms in the ring.

2. The method of claim 1, wherein each of R¹ and R² is hydrogen.

3. The method of claim 1, wherein said Z is oxygen.

4. The method of claim 1, wherein R³ and R⁴ together with the nitrogen atom they are attached to form a substituted ring.

5. The method of claim 1, wherein the compound of Formula I is selected from the group consisting of: N-[2-(2-Morpholin-4-yl-2-oxo-ethylsulfanyl)-benzothiazol-6-yl]-3-phenyl-propionamide; N[2-(2-oxo-2-piperidin-1-yl-ethylsulfanyl)-benzothiazol-6-yl]-propionamide; 1'[2-(Benzooxazol-2-ylsulfanyl)-acetyl]-[1,4']bipiperidinyl-4'-carboxylic acid amide; 3-(Benzothiazol-2-ylsulfanyl)-1-benzyl-pyrrolidine-2, 5-dione; 2-Methyl-N-[2-(2-morpholin-4-yl-2-oxo-ethylsulfanyl)-benzothiazol-6-yl]-benzamide; 2,4-Dichloro-N-[-(2-(2-morpholin-4-yl-2-oxo-ethylsulfanyl)-benzothiazol-6-yl]-benzamide; 1-(3,4-Dihydro-1H-isoquinolin-2-yl)-2-(6-ethoxy-benzothiazol-2-ylsulfanyl)-ethanone; 2-(1H-Benzoimidazol-2-ylsulfanyl)-1-[4-(4-fluoro-phenyl)-piperazin-1-yl]-ethanone; 1'-[2-(Benzothiazol-2-ylsulfanyl) -acetyl]-[1,4']bipiperidinyl-4'-carboxylic acid amide; 2-(6-Ammo-benzothiazol-2-ylsulfanyl)-1-(4-benzyl-piperazin-1-yl)-ethanone; 2-(Benzooxazol-2-ylsulfanyl)-1-(4-benzyl-piperazin-1-yl) -ethanone; 1-[3-(2-Methoxy-benzoyl)-piperidin-1-yl]-2-(5-methyl-1H-benzoimidazol-2-ylsulfanyl)-ethanone; 3-Methyl-N-[2-(2-morpholin-4-yl-2-oxo-ethylsulfanyl)-benzothiazol-6-yl]-benzamide; 2-(6-Ethoxy-benzothiazol-2-ylsulfanyl)-1-(4-phenyl-piperazm-1-yl)-ethanone; 2-Diethylcarbamoylmethylsulfanyl-benzoimidazole-1-carboxylic acid cyclohexylamide; 2-(6-Ammo-benzothiazol-2-ylsulfanyl)-1-morpholin-4-yl-ethanone; 2-(6-{[1-(4-Bromo-phenyl)-meth-(E)-ylidene]-amino}-benzothiazol-2-ylsulfanyl)-1-morpholm-4-yl-ethanone; 2-(6-{[1-(4-Chloro -phenyl)-meth-(E)-ylidene]-amino}-benzothiazol-2-ylsulfanyl)-1-morpholm-4-yl-ethanone; 2-(6-{[1-Anthracen-9-yl-meth-(E)-ylidene]-amino}-benzothiazol-2-ylsulfanyl)-1-morpholm-4-yl-ethanone; 2-Bromo-N-[2-(2-morpholin-4-yl-2-oxo-ethylsulfanyl)-benzothiazol-6-yl]-benzamide; N-[2-(2-Morpholin-4-yl-2-oxo-ethylsulfanyl)-benzothiazol-6-yl]-benzamide; 4-Butoxy-N-[2-(2-morpholm-4-yl-2-oxo-ethylsulfanyl)-benzothiazol-6-yl]-benzamide; 1-Morpholm-4-yl-2-(6-{[1-[5-(1-phenyl-1H-tetrazol-5-ylsulfanyl)-furan-2-yl]-meth-(E)-ylidene]-amino}-benzothiazol-2-ylsulfanyl)-ethanone; 2-(6-{[1-(2,6-Dichloro-phenyl)-meth-(E)-ylidene]-amino}-benzothiazol-2-ylsulfanyl)-1-morpholm-4-yl-ethanone; 2-(6-{[1-(4-Iodo-phenyl)-meth-(E)-ylidene]-amino}-benzothiazol-2-ylsulfanyl)-1-morpholin-4-yl-ethanone; 2-(6-{[1-(4-Fluoro-phenyl)-meth-(E)-ylidene]-amino}-benzothiazol-2-ylsulfanyl)-1-morpholin-4-yl-ethanone; 2-Fluoro-N-[2-(2-morpholin-4-yl-2-oxo-ethylsulfanyl)-benzothiazol-6-yl]-benzamide; 2-Methoxy-N-[2-(2-morpholin-4-yl-2-oxo-ethylsulfanyl)-benzothiazol-6-yl]-benzamide; 3,4-Dichloro-N-[2-(2-morpholin-4-yl-2-oxo-ethylsulfanyl)-benzothiazol-6-yl]-benzamide; 2-[6-(1,3-Dioxo-1,3-dihydro-isoindol-2-yl)-benzothiazol-2-ylsulfanyl]-N,N-diethyl-acetamide; 2-(6-Amino -benzothiazol-2-ylsulfanyl)-N-[2-(2-morpholin-4-yl-2-oxo-ethylsulfanyl)-benzothiazol-6-yl]-acetamide; Cyclohexanecarboxylic acid [2-(2-morpholin-4-yl-2-oxo-ethylsulfanyl)-benzothiazol-6-yl]-amide; 2-(1-Methyl-1H-imidazol-2-ylsulfanyl)-N-[2-(2-morpholin-4-yl-2-oxo -ethylsulfanyl)-benzothiazol-6-yl]-acetamide; 2-(Benzothiazol-2-ylsulfanyl)-N-[2-(2-morpholin-4-yl-2-oxo-ethylsulfanyl)-benzothiazol-6-yl]-acetamide; 2-(4,5-Diphenyl-4H-[1,2,4 ] triazol-3-ylsulfanyl)-N-[2-(2-morpholin-4-yl-2-oxo-ethylsulfanyl)-benzothiazol-6-yl]-acetamide; 2-(4-Methyl-5-naphthalen-1-ylmethyl-4H-[1,2,4] triazol-3-ylsulfanyl)-N-[2-(2-morpholin-4-yl-2-oxo -ethylsulfanyl)-benzothiazol-6-yl]-acetamide; 2-(4-Methyl-5-phenyl-4H-[1,2,4] triazol-3-ylsulfanyl)-N-[2-(2-morpholin-4-yl-2-oxo-ethylsulfanyl)-benzothiazol-6-yl]-acetamide; N-[2- (2-Morpholin-4-yl-2-oxo-ethylsulfanyl)-benzothiazol-6-yl]-2-naphthalen-1-yl-acetamide; 1-(4-Benzothiazol-2-yl-piperazm-1-yl)-2-(6-ethoxy-benzothiazol-2-ylsulfanyl)-ethanone; 2-(6-Ammo -benzothiazol-2-ylsulfanyl)-1-(4-benzothiazol-2-yl-piperazin-1-yl)-ethanone; 2-(Benzothiazol-2-ylsulfanyl)-1-piperidm-1-yl-ethanone; 2-(1H-Benzoimidazol-2-ylsulfanyl)-1-morpholin-4-yl-ethanone; 1-Azepan-1-yl-2-(1H-benzoimidazol-2-ylsulfanyl)-ethanone; 2-(1H-Benzoimidazol-2-ylsulfanyl)-1-(4-methyl-piperidin-1-yl)-ethanone; 2-(1H-Benzoimidazol-2-ylsulfanyl)-1-pyrrolidin-1-yl-ethanone; 2-(1H-Benzoimidazol-2-ylsulfanyl)-1-(4-phenyl-piperazin-1-yl)-ethanone; 2-(Benzooxazol-2-ylsulfanyl)-1-(3,4-dihydro-1H-isoquinolin-2-yl)-ethanone; 2-(2-Oxo-2-piperidin-1-yl-ethylsulfanyl)-benzooxazole-5-carboxylic acid; 2-(6-Nitro-benzothiazol-2-ylsulfanyl)-1-piperidin-1-yl-ethanone; 1-(4-Benzothiazol-2-yl-piperazin-1-yl) -2-(benzothiazol-2-ylsulfanyl)-ethanone; 2-(1-Phenyl-1H-benzoimidazol-2-ylsulfanyl)-1-(4-phenyl-piperazm-1-yl) -ethanone; 2-(6-Nitro-benzothiazol-2-ylsulfanyl)-1-(4-phenyl-piperazin-1-yl)-ethanone; 2-[5-(Benzothiazol-2-ylsulfanylmethyl)-[1,3,4] oxadiazol-2-ylsulfanyl]-N-cyclohexyl-acetamide; N-{2-[2-Oxo-2-(4-phenyl-piperazin-1-yl)-ethylsulfanyl]-benzothiazol-6-yl}-propionamide; 2-(6-Nitro-benzothiazol-2-ylsulfanyl)-1-pyrrolidm-1-yl-ethanone; 4-Methyl-N-[2-(2-oxo-2-piperidm-1-yl-ethylsulfanyl)-benzothiazol-6-yl]-benzamide; N-{2-[2-Oxo- 2-(4-phenyl-piperazin-1-yl)-ethylsulfanyl]-benzothiazol-6-yl}-acetamide; 4-Chloro-N-[2-(2-oxo-2-pyrrolidin-1-yl-ethylsulfanyl)-benzothiazol-6-yl]-benzamide; 2-(6-Ammo-benzothiazol-2-ylsulfanyl)-1-pyrrolidin-1-yl-ethanone; 3-(4-Benzothiazol-2-yl-piperazin-1-yl)-1-(4-fluoro-phenyl)-pyrrolidine-2,5-dione; 2-(1H-Benzoimidazol-2-ylsulfanyl)-1-(3,4-dihydro-1H-isoquinolm-2-yl)-ethanone; N,N-Diethyl-2-(5-methyl-1H-benzoimidazol-2-ylsulfanyl)-acetamide; 2-(Benzothiazol-2-ylsulfanyl)-1-pyrrolidin-1-yl-ethanone; 3,4-Dimethoxy-N-[2-(2-morpholin-4-yl-2-oxo-ethylsulfanyl)-benzothiazol-6-yl]-benzamide; 2-Bromo-N-[2-(2-oxo-2-pyrrolidin-1-yl -ethylsulfanyl)-benzothiazol-6-yl[-benzamide; 1-]2-(Benzothiazol-2-ylsulfanyl)-acetyl]-piperidme-4-carboxylic acid amide; 1-[2-(Benzooxazol-2-ylsulfanyl)-acetyl]-piperidme-4-carboxylic acid amide; 1-[2-(1H-Benzoimidazol-2-ylsulfanyl)-acetyl]-piperidine-4-carboxylic acid amide; 1'-[2-(4-Ethyl-5-phenyl-4H-[1,2,4]triazol-3-ylsulfanyl)-acetyl]-[1,4'] bipiperidmyl -4'-carboxylic acid amide; 1'-[2-(1H-Benzoimidazol-2-ylsulfanyl)-acetyl]-[1,4'] bipiperidmyl-4'-carboxylic acid amide; 2-(Benzothiazol-2-ylsulfanyl)-1-[4-(4-fluoro-phenyl)-piperazin-1-yl]-ethanone; 1-(4-Benzhydryl-piperazin-1-yl)-2-(benzothiazol-2-ylsulfanyl)-ethanone; 1-[4-(3-Chloro-phenyl)-piperazin-1-yl]-2-(6-nitro-benzothiazol-2-ylsulfanyl)-ethanone; 2-(5-Chloro-benzooxazol-2-ylsulfanyl)-1-morpholm-4-yl-ethanone; N-{2-[2-OxO-2-(4-phenyl-piperazin-1-yl)-ethylsulfanyl]-benzothiazol-6-yl}-butyramide; 2-(Benzooxazol-2-ylsulfanyl)-1-(4-phenyl-piperazm-1-yl)-ethanone; 2-(6-Amino-benzothiazol-2-ylsulfanyl)-1-[4-(4-chloro-phenyl) -piperazm-1-yl]-ethanone; 2-(Benzooxazol-2-ylsulfanyl)-1-[4-(4-p-tolyl-phthalazin-1-yl)-piperazin-1-yl]-ethanone; 2-{1[(2, 6-Dimethyl-phenyl-carbamoyl)-methyl]-1H-benzoimidazol-2-ylsulfanyl}-acetamide; 2-(Benzooxazol-2-ylsulfanyl)-1-[4-(4-chloro-phenyl)-piperazin-1-yl]-ethanone; 1-(3,4-Dihydro-1H-isoquinolm-2-yl)-2-(1-methyl-1H-benzoimidazol-2-ylsulfanyl)-ethanone; and 2-(1-Benzenesulfonyl-1H-benzoimidazol-2-ylsulfanyl)-1-pyrrolidin-1-yl-ethanone.

6. The method of claim 1, wherein the compound of Formula I is 1'-[2-(Benzooxazol-2-ylsulfanyl)-acetyl]-[1,4'] bipiperidmyl-4'-carboxylic acid amide.

7. The method of claim 1, wherein the mammal is a human.

8. The method of claim 1, wherein said Dengue virus is selected from the group consisting of DEN-I, DEN-2, DEN-3, and DEN-4.

9. The method of claim 1, wherein infection causes Dengue fever.

10. The method of claim 9, wherein said Dengue fever is selected from the group consisting of classical dengue fever, dengue hemorrhagic fever syndrome, and dengue shock syndrome.

11. The method of claim 1, which further comprises co-administration of at least one agent selected from the group consisting of antiviral agent, vaccine, and interferon.

12. The method of claim 11, wherein said interferon is pegylated.

13. The method of claim 1, wherein the compound of Formula I is selected from the group consisting of: N-[2-(2-Morpholin-4-yl-2-oxo-ethylsulfanyl)-benzothiazol-6-yl]-3-phenylpropionamide; N-[2-(2-Oxo-2-piperidin-1-yl-ethylsulfanyl)-benzothiazol-6-yl]-propionamide; 1'[2-(Benzooxazol-2-ylsulfanyl)-acetyl]-[1,4'] bipiperidinyl-4'-carboxylic acid amide; 3(Benzothiazol-2-ylsulfanyl)-1-benzyl-pyrrolidine-2,5-dione; 2-Methyl-N-[2-(2-morpholin-4-yl2-oxo-ethylsulfanyl)-benzothiazol-6-yl]-benzamide; 2,4-Dichloro-N-[2-(2-morpholin-4-yl-2-oxo-ethylsulfanyl)-benzothiazol-6-yl]-benzamide; 1-(3,4-Dihydro-1H -isoquinolin-2-yl)-2-(6-ethoxy-benzothiazol-2-ylsulfanyl)-ethanone; 2-(1H-Benzoimidazol-2-ylsulfanyl)-1-[4-(4-fluorophenyl)-piperazin-1-yl]-ethanone; 1'-[2-(Benzothiazol-2-ylsulfanyl) -acetyl]-[1,4'] bipiperidinyl-4'-carboxylic acid amide; 2-(6-Amino-benzothiazol-2-ylsulfanyl)-1-(4-benzyl-piperazin-1-yl)-ethanone; 2-(Benzooxazol-2-ylsulfanyl)-1-(4-benzyl-piperazin-1-yl)-ethanone; 1-[3-(2-Methoxy-benzoyl)-piperidin-1-yl]-2-(5-methyl-1H-benzoimidazol-2-ylsulfanyl)-ethanone; 3-Methyl-N-[2(2-morpholin-4-yl-2-oxo -ethylsulfanyl)-benzothiazol-6-yl]-benzamide; and 2-(6-Ethoxy-benzothiazol-2-ylsulfanyl)-1-(4-phenyl-piperazin-1-yl)-ethanone.

* * * * *